United States Patent
Xu

(10) Patent No.: US 11,000,482 B2
(45) Date of Patent: May 11, 2021

(54) FABRICATION OF A SURAMIN-LOADED NANOPARTICLE AND ITS APPLICATION

(71) Applicant: UNIVERSITY OF SOUTH CAROLINA, Columbia, SC (US)

(72) Inventor: Peisheng Xu, Chapin, SC (US)

(73) Assignee: University of South Carolina, Columbia, SC (US)

(*) Notice: Subject to any disclaimer, the term of this patent is extended or adjusted under 35 U.S.C. 154(b) by 0 days.

(21) Appl. No.: 16/568,865

(22) Filed: Sep. 12, 2019

(65) Prior Publication Data

US 2020/0155472 A1     May 21, 2020

Related U.S. Application Data

(60) Provisional application No. 62/770,281, filed on Nov. 21, 2018, provisional application No. 62/807,049, filed on Feb. 18, 2019.

(51) Int. Cl.

| | |
|---|---|
| *A61K 9/51* | (2006.01) |
| *A61K 31/17* | (2006.01) |
| *A61P 35/00* | (2006.01) |
| *A61K 31/704* | (2006.01) |

(52) U.S. Cl.
CPC .......... *A61K 9/5123* (2013.01); *A61K 9/5192* (2013.01); *A61K 31/17* (2013.01); *A61K 31/704* (2013.01); *A61P 35/00* (2018.01)

(58) Field of Classification Search
None
See application file for complete search history.

(56) References Cited

U.S. PATENT DOCUMENTS

| | | |
|---|---|---|
| 8,809,277 B2 | 8/2014 | Xu et al. |
| 8,945,629 B2 | 2/2015 | Radosz et al. |
| 9,149,535 B2 | 10/2015 | Xu et al. |
| 9,993,439 B2 * | 6/2018 | Gu .................. A61K 31/69 |
| 2010/0203149 A1 | 8/2010 | Radosz et al. |

(Continued)

FOREIGN PATENT DOCUMENTS

WO    WO 2007/120504    10/2007

OTHER PUBLICATIONS

Medscape dosing, indications, interactions, adverse effects, and more product information, obtained Oct. 20, 2020. (Year: 2020).*

(Continued)

*Primary Examiner* — Melissa S Mercier
(74) *Attorney, Agent, or Firm* — Dority & Manning, P.A.

(57) ABSTRACT

A nanoparticle system for the treatment of metastatic cancer is provided. The nanoparticle system includes a plurality of nanoparticles. Each of the nanoparticles includes a biodegradable matrix, a polysulphonated naphthylurea, and a chemotherapeutic agent. The biodegradable matrix can be a natural polysaccharide, a protein, a peptide, or a derivative thereof. Further, the polysulphonated naphthylurea can include suramin or a pharmaceutically acceptable salt thereof, and the chemotherapeutic agent can include an anthracycline. In addition, each of the nanoparticles has a diameter ranging from about 20 nanometers to about 400 nanometers. A method of forming the nanoparticle system and a method of treating cancer in a mammal with the nanoparticle system are also provided.

18 Claims, 27 Drawing Sheets

(56) References Cited

U.S. PATENT DOCUMENTS

2013/0244953 A1  9/2013  Xu et al.
2014/0011760 A1  1/2014  Xu et al.

OTHER PUBLICATIONS

Akita, et al. "Basic fibroblast growth factor accelerates and improves second-degree burn wound healing" *Wound Rep. Regen.* 16(5) (2008) pp. 635-641.
Beenken, et al. "The FGF family: Biology, pathophysiology and therapy" *Drug Disc.* 8(3) (2009) pp. 235-253.
Bowden, et al. "A phase I/II study of continuous infusion suramin in patients with hormone-refractory prostate cancer: Toxicity and response" *Cancer Chemo. Pharma.* 39(1-2) (1996) pp. 1-8.
Bugge, et al. "Growth and dissemination of Lewis lung carcinoma in plasminogen-deficient mice" *Blood* 90(11) (1997) pp. 4522-4531.
Chen, et al. "Synergistic effects of glycated chitosan with high-intensity focused ultrasound on suppression of metastases in a syngeneic breast tumor model" *Cell Death Dis.* 5:e1178 (2014) pp. 1-9.
Chou, T.C. "Drug combination studies and their synergy quantification using the Chou-Talalay method" *Cancer Res.* 70(2) (2010) pp. 440-446.
Csaba, et al. "Ionically crosslinked chitosan nanoparticles as gene delivery systems: Effect of PEGylation degree on in vitro and in vivo gene transfer" *J. Biomed. Nanotechnol.* 5(2) (2009) pp. 162-171.
Daniele, et al. "FGF receptor inhibitors: Role in cancer therapy" *Curr. Onc. Rep.* 14(2) (2012) pp. 111-119.
Desantis, et al. "Breast cancer statistics, 2013" *CA: Cancer J. Clinic.* 64(1) (2014) pp. 52-62.
Dieci, et al. "Fibroblast growth factor receptor inhibitors as a cancer treatment: From a biologic rationale to medical perspectives" *Cancer Disc.* 3(3) (2013) pp. 264-279.
El-Gibaly, et al. "Novel B melatonin-loaded chitosan microcapsules: In vitro characterization and antiapoptosis efficacy for aflatoxin B1-induced apoptosis in rat liver" *Int'l J. Pharmaceut.* 260(1) (2003) pp. 5-22.
Elkin, et al. "Tail vein assay of cancer metastasis" *Curr. Protoc. Cell Biol.* 12(1) (2001) pp. 19.2.1-19.2.7. (Abstract only).
Elsayed, et al. "Chitosan—Sodium Lauryl Sulfate Nanoparticles as a Carrier System for the In Vivo Delivery of Oral Insulin" *AAPS Pharmscitech* 12(3) (2011) pp. 958-964.
Foekens, et al. "Pleiotropic actions of suramin on the proliferation of human breast-cancer cells in vitro" *Int'l. J. Cancer* 51(3) (1992) pp. 439-444.
Gagliardi, et al. "Uptake of suramin by human microvascular endothelial cells" *Cancer Lett.* 125(1-2) (1998) pp. 97-102.
Gan, et al. "Modulation of surface charge, particle size and morphological properties of chitosan—TPP nanoparticles intended for gene delivery" *Coll. Surf. B Biointer.* 44(2-3) (2005) pp. 65-73.
Gao, et al. "GSK-3beta Phosphorylation of Cytoplasmic Dynein Reduces Ndel1 Binding to Intermediate Chains and Alters Dynein Motility" *Traffic* 16(9) (2015) pp. 941-961.
Hanahan, et al. "Patterns and emerging mechanisms of the angiogenic switch during tumorigenesis" *Cell* 86(3) (1996) pp. 353-364.
Haugsten, et al. "Roles of fibroblast growth factor receptors in carcinogenesis" *Molecul. Canc. Res.* 8(11) (2010) pp. 1439-1452.
He, et al. "Mussel-inspired PLGA/polydopamine core-shell nanoparticle for light induced cancer thermochemotherapy" *Acta Biomater.* 59 (2017) pp. 181-191.
Hierro, et al. "Fibroblast Growth Factor (FGF) Receptor/FGF Inhibitors: Novel Targets and Strategies for Optimization of Response of Solid Tumors" *Semin. Oncol.* 42(6) (2015) pp. 801-819.
Holland, et al. "Basic fibroblast growth factor induces cell migration and proliferation after glia-specific gene transfer in mice" *PNAS* 95(3) (1998) pp. 1218-1223.

Huang, et al. "Monovalent salt enhances colloidal stability during the formation of chitosan/tripolyphosphate microgels" *Langmuir* 27(17) (2011) pp. 10392-10399.
Ichikawa, et al. "Cardiotoxicity of doxorubicin is mediated through mitochondrial iron accumulation" *J. Clin. Invest.* 124(2) (2014) pp. 617-630.
Jonassen, et al. "Stability of chitosan nanoparticles cross-linked with tripolyphosphate" *Biomacromolecules* 13(11) (2012) pp. 3747-3756.
Ke, et al. "pH-sensitive polycarbonate micelles for enhanced intracellular release of anticancer drugs: A strategy to circumvent multidrug resistance" *Polym. Chem.* 5(7) (2014) pp. 2621-2628.
Khanna, et al. "Modeling metastasis in vivo" *Carcinogenesis* 26(3) (2005) pp. 513-523.
Klein-Soyer, et al. "Behavior of confluent endothelial cells after irradiation. Modulation of wound repair by heparin and acidic fibroblast growth factor" *Biol. Cell* 68(3) (1990) pp. 231-238.
Kosarek, et al. "Phase I evaluation of low-dose suramin as chemosensitizer of doxorubicin in dogs with naturally occurring cancers" *J. Vet. Int. Med.* 20(5) (2006) pp. 1172-1177.
Kumar, et al. "Fibroblast growth factor receptor inhibitors" *Curr. Pharmac. Des.* 19(4) (2013) pp. 687-701.
Ledzewicz, et al. "Optimal and suboptimal protocols for a mathematical model for tumor anti-angiogenesis in combination with chemotherapy" *Math. Biosci. Eng.* 8(2) (2011) pp. 307-323.
Lelievre, et al. "Altered topoisomerase I and II activities in suramin-resistant lung fibrosarcoma cells" *Mol. Pharm.* 7(5) (1995) pp. 898-906.
Li, et al. "Nuclear basic fibroblast growth factor regulates triple-negative breast cancer chemo-resistance" *Breast Cancer Res.* 17:91 (2015) pp. 1-16.
Li, et al. "Suramin inhibits cell proliferation in ovarian and cervical cancer by downregulating heparanase expression" *Cancer Cell Int'l.* 15:52 (2015) pp. 1-11.
Lu, et al. "Targeted delivery of Doxorubicin by folic acid-decorated dual functional nanocarrier" *Mol. Pharm.* 11(11) (2014) pp. 4164-4178.
McGeary, et al. "Suramin: Clinical uses and structure-activity relationships" *Mini Rev. Med. Chem.* 8(13) (2008) pp. 1384-1394. (Abstract only).
Miranda, et al. "Hfe deficiency increases susceptibility to cardiotoxicity and exacerbates changes in iron metabolism induced by doxorubicin" *Blood* 102(7) (2003) pp. 2574-2580.
Park, et al. "Chemical Conjugate of Low Molecular Weight Heparin and Suramin Fragment Inhibits Tumor Growth Possibly by Blocking $VEGF_{165}$" *Mol. Pharm.* 12(11) (2015) pp. 3935-3942.
Plaksin, et al. "Reversal of the metastatic phenotype in Lewis lung carcinoma cells after transfection with syngeneic H-2Kb gene" *PNAS* 85(12) (1988) pp. 4463-4467.
Rashid, et al. "Is tail vein injection a relevant breast cancer lung metastasis model?" *J. Thorac. Dis.* 5(4) (2013) pp. 385-392.
Redig, et al. "Breast cancer as a systemic disease: A view of metastasis" *J. Int. Med.* 274(2) (2013) pp. 113-126.
Rogelj, et al. "Basic fibroblast growth factor is an extracellular matrix component required for supporting the proliferation of vascular endothelial cells and the differentiation of PC12 cells" *J. Cell Biol.* 109(2) (1989) pp. 823-831.
Sandler, et al. "Paclitaxel-carboplatin alone or with bevacizumab for non-small-cell lung cancer" *New Engl. J. Med.* 355(24) (2006) pp. 2542-2550.
Santander-Ortega, et al. "Chitosan nanocapsules: Effect of chitosan molecular weight and acetylation degree on electrokinetic behaviour and colloidal stability" *Coll. Surf. B Biointer.* 82(2) (2011) pp. 571-580.
Singla, et al. "Combined treatment with paclitaxel and suramin prevents the development of metastasis by inhibiting metastatic colonization of circulating tumor cells" *Clin. Exper. Metast.* 31(6) (2014) pp. 705-714. (Abstract only).
Smith, et al. "Acute renal failure in a patient receiving treatment with suramin" *Am. J. Clin. Onc.* 20(4) (1997) pp. 433-434.
Song, et al. "Low-dose suramin enhanced paclitaxel activity in chemotherapy-naive and paclitaxel-pretreated human breast xenograft tumors" *Clin. Cancer Res.* 10 (2004) pp. 6058-6065.

(56) References Cited

OTHER PUBLICATIONS

Song, et al. "Nontoxic doses of suramin enhance activity of paclitaxel against lung metastases" *Cancer Res.* 61(16) (2001) pp. 6145-6150.
Song, et al. "Fibroblast growth factors: an epigenetic mechanism of broad spectrum resistance to anticancer drugs" *PNAS* 97(15) (2000) pp. 8658-8663.
Steeg, et al. "Metastasis: A therapeutic target for cancer" *Oncology* 5(4) (2008) pp. 206-219.
Takano, et al. "Suramin, an anticancer and angiosuppressive agent, inhibits endothelial cell binding of basic fibroblast growth factor, migration, proliferation, and induction of urokinase-type plasminogen activator" *Cancer Res.* 54(10) (1994) pp. 2654-2660.
Tomlinson, et al. "Fibroblast growth factor receptor 1 promotes proliferation and survival via activation of the mitogen-activated protein kinase pathway in bladder cancer" *Cancer Res.* 69(11) (2009) pp. 4613-4620.
Tu, et al. "Phase I study of suramin combined with doxorubicin in the treatment of androgen-independent prostate cancer" *Clin. Cancer Res.* 4(5) (1998) pp. 1193-1201.
Turdi, et al. "Amidization of doxorubicin alleviates doxorubicin-induced contractile dysfunction and reduced survival in murine cardiomyocytes" *Toxicol. Lett.* 178(3) (2008) pp. 197-201.
Turner, et al. "Fibroblast growth factor signalling: From development to cancer" *Cancer* 10(2) (2010) pp. 116-129.
Waltenberger, et al. "Suramin is a potent inhibitor of vascular endothelial growth factor. A contribution to the molecular basis of its antiangiogenic action" *J. Mol. Cellul. Card.* 28(7) (1996) pp. 1523-1529.
Wan, et al. "Tumor metastasis: Moving new biological insights into the clinic" *Nature Med.* 19(11) (2013) 1450-1464.
Wang, et al. "Cellular uptake of nanoparticles by membrane penetration: A study combining confocal microscopy with FTIR spectroelectrochemistry" *ACS Nano* 6(2) (2012) pp. 1251-1259.
Zaniboni, A. "Suramin the discovery of an old anticancer drug" *Med. Onc. Tumor Pharma.* 7(4) (1990) pp. 287-290. (Abstract only).
Zhang, et al. "Nontoxic doses of suramin enhance activity of doxorubicin in prostate tumors" *J. Pharma. Exp. Ther.* 299(2) (2001) pp. 426-433.

\* cited by examiner

FABRICATION OF A SURAMIN-LOADED NANOPARTICLE AND ITS APPLICATION

RELATED APPLICATIONS

The present application claims priority to U.S. Provisional Application Ser. No. 62/770,281, filed on Nov. 21, 2018, and to U.S. Provisional Application Ser. No. 62/807,049, filed on Feb. 18, 2019, each of which is incorporated herein in its entirety by reference thereto.

BACKGROUND OF THE INVENTION

Breast cancer is the most common cancer among women worldwide, and metastasis is the major cause of human deaths related to cancer. Metastasis involves multiple steps, including cell invasion from the primary tumor, intravasation and extravasation in the circulation system, and growth in the distant location. Ideally, the most effective way of treating metastatic cancer is to kill cancer cells before their dissemination from the primary cancer site. However, due to the lack of clinically effective tools available to accurately detecting small tumor mass and to kill 100% of cancer cells, many patients eventually die from cancer metastasis. When a breast cancer patient is diagnosed with distant metastasis, the five-year survival rate drops sharply from 98.6% to 23.4%. Currently, various treatments are available for patients with different stages of metastasis. However, at the early stage before the diagnosis of circulating tumor cells (CTC), the only FDA-approved treatments include prophylactic and vaccination. Once a patient is diagnosed with CTC, or even micro-metastasis, surgery or radiation plus systemic therapy will be applied. For high risk patients, metronomic chemotherapy and anti-angiogenesis might be necessary.

Angiogenesis, a hallmark of malignant disease, is a process involving the formation of new blood vessels based on the original blood vessels, where angiogenesis is critical for tumor progression. CTCs up-regulate several pro-angiogenic factors, such as vascular endothelial growth factor (VEGF) and basic fibroblast growth factor (bFGF), to adapt to the new tumor microenvironments. The combination bevacizumab, an inhibitor of VEGF, with paclitaxel/carboplatin has been shown to significantly increase the median number of survival months for patients diagnosed with metastatic colorectal cancer or advanced non-small cell lung cancer in a phase III trial. However, for patients with late-stage breast cancer, the best treatment so far only provides an increase in survival of a few months. FGFs and their receptors (FGFRs) play crucial roles in many fundamental processes from embryogenesis to adult life, such as proliferation, differentiation, migration, angiogenesis, and wound healing. Like many other mitogens, FGFs act like a double-edged sword and deregulate the signaling causing various types of human cancers, including lung, breast, ovarian, and prostate cancers. Therefore, FGFs/FGFRs have been extensively studied as potential targets for cancer treatment, and many selective or non-selective pharmaceutical inhibitors for FGFs and FGFRs have been developed.

Suramin (SM), a polysulphonated naphthylurea that non-specifically inhibits VEGF and bFGF, is a drug used in the treatment of African sleeping sickness and river blindness therapy and has been explored in various clinical trials for cancer therapy. However, SM was eventually withdrawn from the market due to its narrow therapeutic window and the side effects associated with multiple targets. Suramin has also been reported as an anti-angiogenesis agent. SM has been shown to reverse the FGF-induced drug resistance at a concentration of 1-17 μM in human prostate PC3 cells in the presence of doxorubicin (DOX), a chemotherapeutic agent. The combination of SM and various chemotherapeutic agents have been proven effective in many mice models and entered clinical trials. For instance, the combination of SM and paclitaxel has been shown to inhibit the brain metastatic cancer at the dose of SM at 10 mg/kg and PTX at 10 mg/kg. However, although SM has been shown to have a direct impact on cancer cells, high doses of SM not only cause cytotoxic effects and renal damage but also initiate tolerance response, which is not ideal. In addition, DOX is known to cause cardiac damage.

As such, a need exists for a drug delivery system for suramin and/or other polysulphonated naphthylureas and doxorubicin and/or other chemotherapeutic agents that can treat metastatic cancers without being toxic.

SUMMARY OF THE INVENTION

According to one particular embodiment of the present invention, a nanoparticle system is provided. The nanoparticle system includes a plurality of nanoparticles, where each of the nanoparticles includes a biodegradable matrix, a polysulphonated naphthylurea, and a chemotherapeutic agent. In addition, each of the nanoparticles has a diameter ranging from about 20 nanometers to about 400 nanometers.

In one embodiment, the biodegradable matrix can include a natural polysaccharide, a protein, a peptide, or a derivative thereof. For instance, the biodegradable matrix can include glycol chitosan, chitosan, collagen, gelatin, or protamine.

In another embodiment, the polysulphonated naphthylurea can include suramin or a pharmaceutically acceptable salt thereof. For example, the polysulphonated naphthylurea can include suramin sodium salt.

In still another embodiment, the chemotherapeutic agent can include an anthracycline. Further, the chemotherapeutic agent can include doxorubicin.

In yet another embodiment, a ratio of the concentration of the polysulphonated naphthylurea to the concentration of the chemotherapeutic agent can range from about 2 to about 100.

In one more embodiment, the polysulphonated naphthylurea can be present at a concentration ranging from about 0.1 micromolar to about 200 micromolar.

In an additional embodiment, the chemotherapeutic agent can be present at a concentration ranging from about 0.025 micromolar to about 20 micromolar.

According to another particular embodiment of the present invention, a method of forming a nanoparticle system is provided. The method includes forming a first solution that includes a first water-based salt solution having a pH ranging from about 6 to about 7.2 and a biodegradable matrix; forming a second solution that includes a second water-based salt solution having a pH ranging from about 6 to about 7.2 and a polysulphonated naphthylurea or a pharmaceutically acceptable salt thereof forming a third solution that includes a double-distilled water and a chemotherapeutic agent; combining the second solution and the third solution to form a fourth solution; and adding the fourth solution to the first solution to form a plurality of nanoparticles.

In one embodiment, the biodegradable matrix can include a natural polysaccharide, a protein, a peptide, or a derivative thereof.

In another embodiment, the polysulphonated naphthylurea can include suramin or a pharmaceutically acceptable salt thereof.

In still another embodiment, the chemotherapeutic agent can include an anthracycline.

In yet another embodiment, the concentration of the biodegradable matrix in the first solution can range from about 1 milligram/milliliter to about 4 milligrams/milliliter.

In one more embodiment, the concentration of the polysulphonated naphthylurea in the second solution can range from about 0.08 milligrams/milliliter to about 0.7 milligrams/milliliter.

In an additional embodiment, the concentration of the chemotherapeutic agent in the third solution can range from about 0.25 milligrams/milliliter to about 2 milligrams/milliliter.

According to still another embodiment of the present invention, a method of treating cancer in a mammal is provided. The method includes introducing a nanoparticle system that includes a plurality of nanoparticles to a cancerous tumor in tissue of the mammal, wherein each of the plurality of nanoparticles includes a biodegradable matrix, a polysulphonated naphthylurea, and a chemotherapeutic agent, wherein each of the nanoparticles has a diameter ranging from about 20 nanometers to about 400 nanometers.

In one embodiment, the biodegradable matrix can include a natural polysaccharide, a protein, a peptide, or a derivative thereof, the polysulphonated naphthylurea can include suramin or a pharmaceutically acceptable salt thereof, and the chemotherapeutic agent can include an anthracycline. Further, a ratio of the concentration of the polysulphonated naphthylurea to the concentration of the chemotherapeutic agent ranges from about 2 to about 100.

Other features and aspects of the present invention are set forth in greater detail below.

Figure 1:
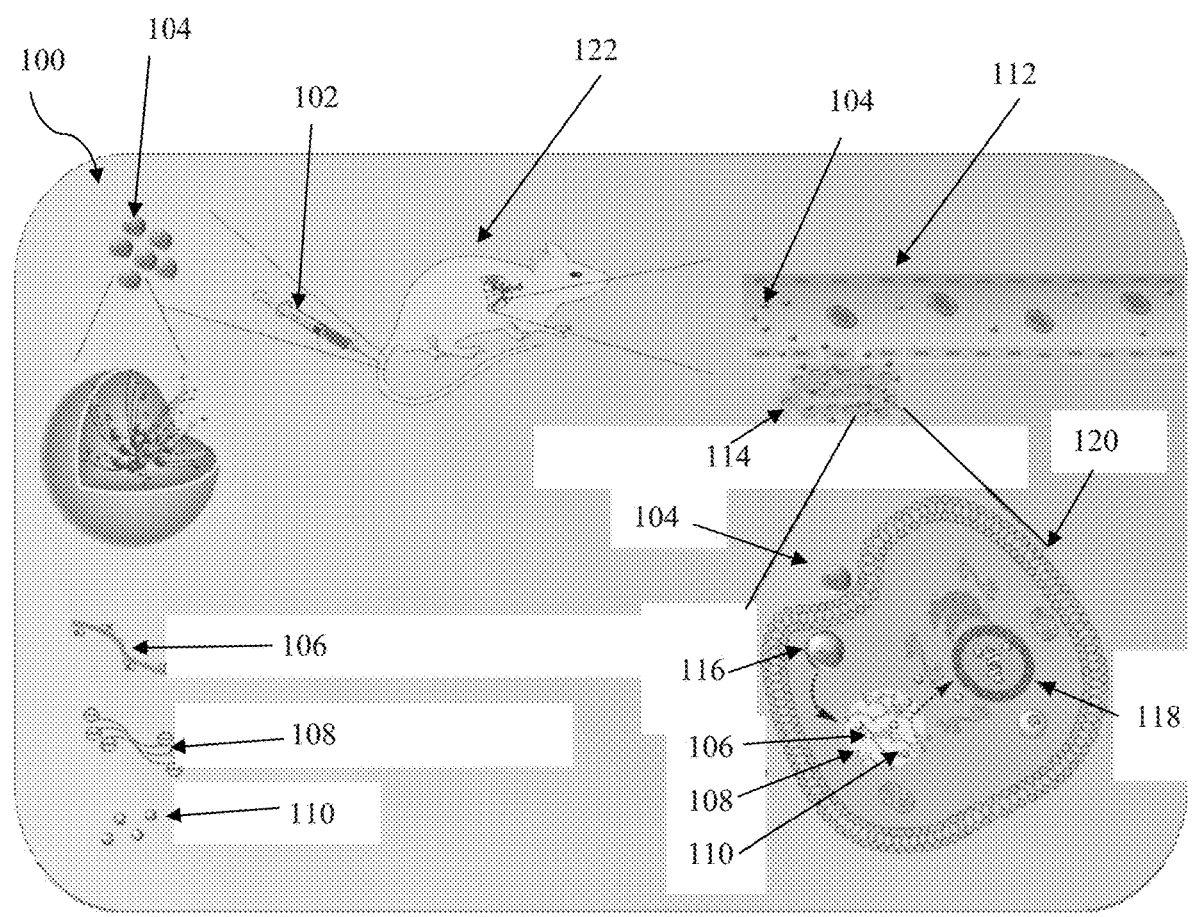
FIG. 1 illustrates the assembly of the suramin loaded nanoparticles contemplated by the present invention and the action of the nanoparticles in treating breast cancer lung metastasis.
Figure 2A:
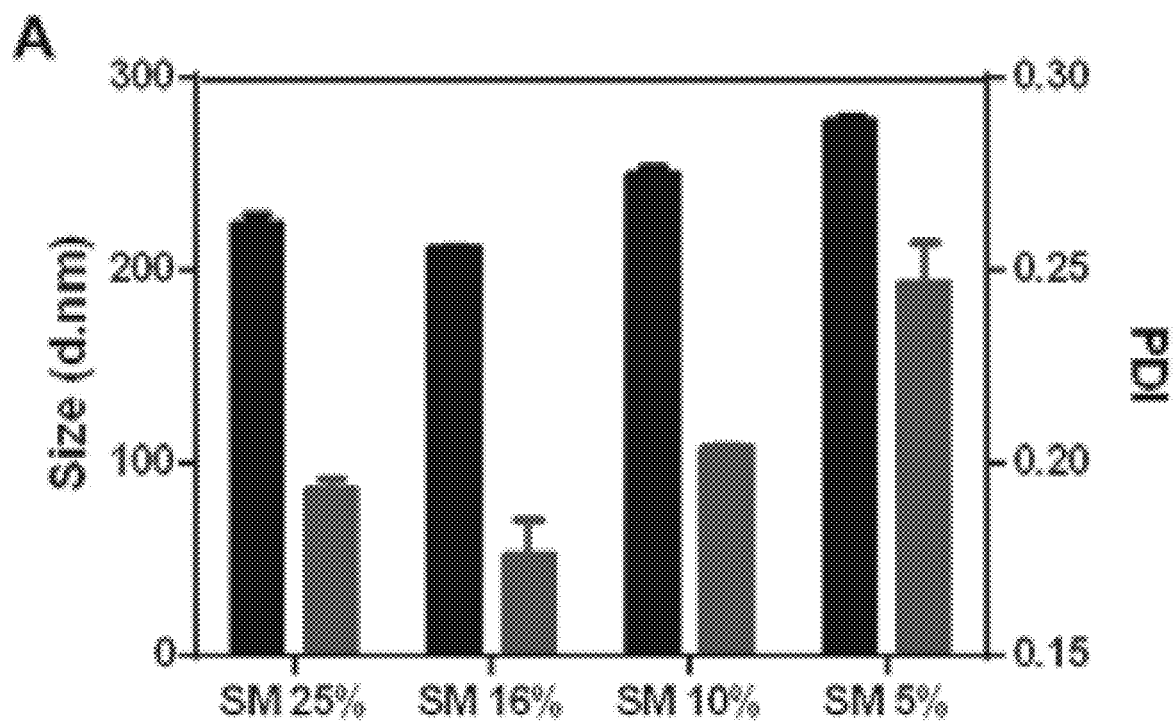
FIG. 2A illustrates the effect of the amount of suramin (SM) in the final formulation on nanoparticle size (hydrodynamic) on the left and polydispersity index (PDI) size on the right.
Figure 2B:
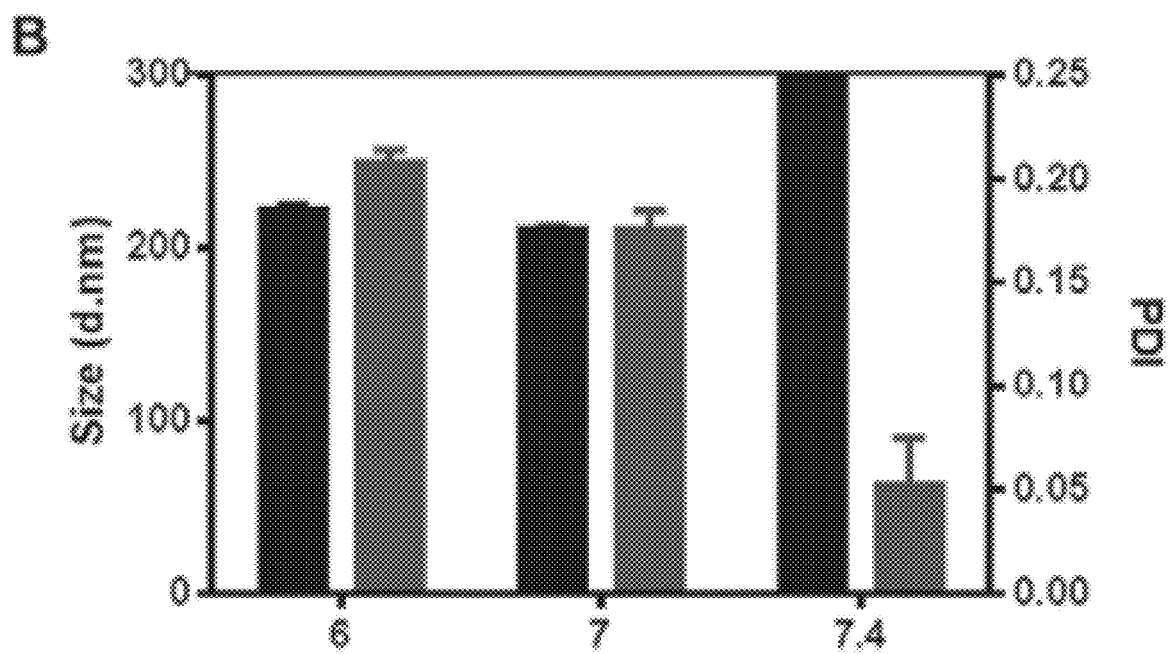
FIG. 2B illustrates the effect of the pH on nanoparticle size (hydrodynamic) on the left and polydispersity index (PDI) size on the right.
Figure 2C:
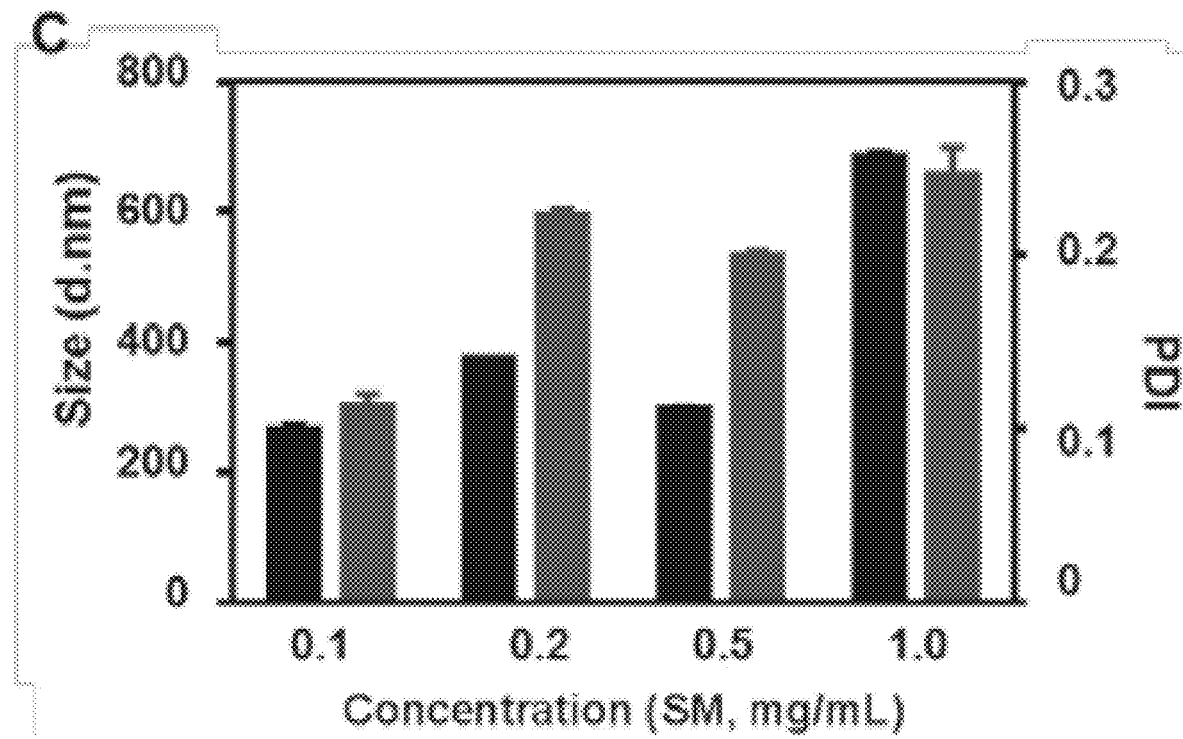
FIG. 2C illustrates the effect of the final suramin (SM) concentration on the nanoparticle size (hydrodynamic) on the left and polydispersity index (PDI) size on the right.
Figure 2D:
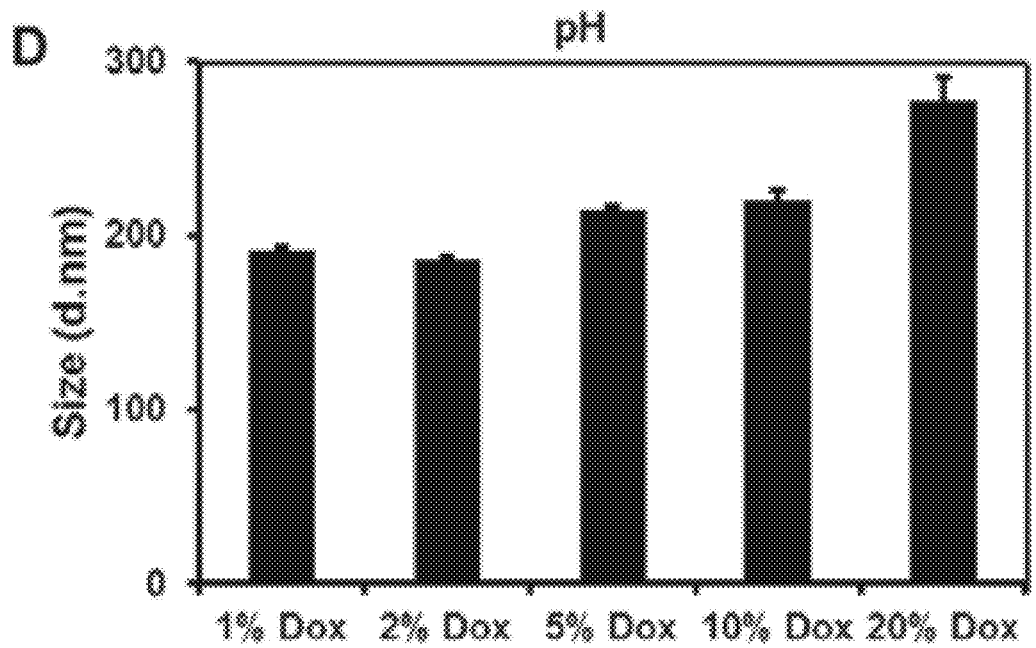
FIG. 2D illustrates the effect of the loading content of doxorubicin (DOX) on the nanoparticle size.

Repeat use of reference characters in the present specification and drawings is intended to represent the same or analogous features or elements of the present invention.

DETAILED DESCRIPTION

Reference now will be made to the embodiments of the invention, one or more examples of which are set forth below. Each example is provided by way of an explanation of the invention, not as a limitation of the invention. In fact, it will be apparent to those skilled in the art that various modifications and variations can be made in the invention without departing from the scope or spirit of the invention. For instance, features illustrated or described as one embodiment can be used on another embodiment to yield still a further embodiment. Thus, it is intended that the present invention cover such modifications and variations as come within the scope of the appended claims and their equivalents. It is to be understood by one of ordinary skill in the art that the present discussion is a description of exemplary embodiments only, and is not intended as limiting the broader aspects of the present invention, which broader aspects are embodied exemplary constructions.

Generally speaking, the present invention is directed to a simple and effective nanoparticle system for the treatment of metastatic cancer without causing renal or cardiac damage traditionally associated with cancer treatments utilizing the components of the nanoparticle system. In one particular embodiment, the nanoparticle system of the present invention can be used in the treatment of breast cancer lung metastasis. The various components of the nanoparticle system of the present invention, the method of forming the nanoparticle system, and the method of treating a mammal with the nanoparticle system are discussed in more detail below.

In particular and referring to FIG. 1, the nanoparticle system 100 of the present invention can include a biodegradable matrix 106, a polysulphonated naphthylurea 108, and a chemotherapeutic agent 110. After the nanoparticle system 100 is formed, the nanoparticle system 100, which can include a plurality of nanoparticles 104 containing the biodegradable matrix 106, the polysulphonated naphthylurea 108, and the chemotherapeutic agent 110, can be injected into a mammal 122 via syringe 102 or other suitable drug delivery means to target tissue 112 (e.g., lung tissue) in which a metastatic tumor 114 is present. The nanoparticles 100 forming the nanoparticle system 104 can then interact with tumor cells 120 whereby the nanoparticles 100 deliver the polysulphonated naphthylurea 108 and the chemotherapeutic agent 110 to the tumor cells 120. As shown in FIG. 1, the nanoparticles 100 are transported within the tumor cell 120 via endosomes 116, after which the biodegradable matrix 106 can degrade to release the polysulphonated naphthylurea 108 and the chemotherapeutic agent 110 to act on the tumor cell nucleus 118 and/or other components of the tumor cell 120.

The biodegradable matrix 106 can include a natural polysaccharide, a protein, a peptide, or a derivative of a natural polysaccharide, a protein, or a peptide. For instance, the biodegradable matrix 106 can include a chitosan, collagen, gelatin, or protamine. In one particular embodiment, the biodegradable matrix can include glycol chitosan, which is a chitosan derivative containing glycol groups at C-6 that is soluble in water at any pH. However, it is also to be understood that any other suitable biodegradable matrix 106 can be used so long as the biodegradable matrix is soluble in water and allows for the transport and subsequent release of the polysulphonated naphthylurea 108 and the chemotherapeutic agent 110 into the tumor cell 120. For instance, chitosan, collagen, gelatin, and protamine, which are all positively charged materials, could also be used as the biodegradable matrix 106.

In addition, the polysulphonated naphthylurea 108 can be suramin or a pharmaceutically acceptable salt thereof. Suramin has the chemical name 8,8'-[carbonylbis[imino-3,1-phenylenecarbonylimino (4-methyl-3,1-phenylene)carbonylimino]]bisnaphthalene-1,3,5-trisulphonic acid and has the molecular formula $C_{51}H_{40}N_6O_{23}S_6$. As used herein, the term "suramin" shall include both suramin and pharmaceutically acceptable salts thereof including, for example, alkaline metal, alkaline earth metal, other non-toxic metals, ammonium and substituted ammonium salts such as, but not limited to, the sodium, potassium, lithium, calcium, magnesium, aluminum, zinc, ammonium, trimethyl ammonium, triethyl ammonium, tetrabutyl ammonium, pyridinium and substituted pyridinium salts. In one particular embodiment, the present invention contemplates the use of suramin sodium salt as the polysulphonated naphthylurea 108.

Further, the chemotherapeutic agent 110 can be an anthracycline. Anthracyclines are a class of chemotherapy drugs that are extracted from *Streptomyces* bacterium. Examples of suitable anthracyclines contemplated by the present invention include doxorubicin, daunorubicin, epirubicin, and idarubicin. In one particular embodiment, the chemotherapeutic agent 110 can be doxorubicin.

By inclusion of the components discussed above, where such components have been found to act synergistically, the present invention contemplates a simple but effective nanoparticle system 104 based on a non-toxic dose of a polysulphonated naphthylurea 108 combined with a chemotherapeutic agent 110 in a nanoparticle 100 containing a biodegradable matrix 106 for the treatment of metastatic cancer, such as metastatic triple negative breast cancer. In one particular embodiment, the nanoparticle system 104 can include glycol chitosan (GCS), suramin (SM), and doxorubicin (DOX), where it has been found that the SM and GCS can form a nanogel due to an electrostatic effect, and the doxorubicin (DOX) can be incorporated into or encapsulated in the resulting nanogel system due to the hydrophilic and hydrophobic interactions between DOX and GCS, as well as the ionic interactions between DOX and SM to yield GCS-SM/DOX nanoparticles. Both the SM and GCS components of the nanoparticle system can exhibit an inhibitory effect on the migration and invasion of, for instance, MDA-MB-231 breast cancer cells, where the SM, delivered at a non-toxic dose, can enhance the anticancer efficacy of DOX both in vitro and in vivo.

Further, by controlling the various concentrations of the individual components and the ratios of the components, the size of the GCS-SM/DOX nanoparticles can be controlled to optimize the effect of the nanoparticles on cancer cells. For instance, the GCS-SM/DOX nanoparticles (or nanoparticles containing other biodegradable matrix materials 106, polysulphonated naphthylureas 108, and chemotherapeutic agents 110 as contemplated by the present invention) can have a diameter ranging from about 20 nanometers (nm) to about 400 nm, such as from about 50 nm to about 375 nm, such as from about 75 nm to about 350 nm, such as from about 100 nm to about 325 nm, such as from about 150 nm to about 300 nm and can also exhibit a spherical morphology. In one particular embodiment, the nanoparticles 100 can have a diameter ranging from about 175 nm to about 225 nm.

Further, the concentration of the polysulphonated naphthylurea 108 can range from about 0.1 micromolar ($\mu$M) to about 200 such as from about 0.25 $\mu$M to about 150 such as from about 0.5 $\mu$M to about 125 such as from about 1 $\mu$M to about 100 such as from about 2.5 $\mu$M to about 50 while the concentration of the chemotherapeutic agent 110 can be greater than 0.005 $\mu$M and can range from about 0.025 $\mu$M to about 20 such as from about 0.05 $\mu$M to about 1.5 such as from about 0.075 $\mu$M to about 1.25 such as from about 0.1 $\mu$M to about 1 $\mu$M. In addition, in some embodiments, the ratio of the concentration of the polysulphonated naphthylurea 108 to the chemotherapeutic agent 110 can range from about 2 to about 100, such as from about 2.5 to about 30, such as from about 3 to about 25, such as from about 3.5 to about 20, where it has been found that such ratios provide a synergistic effect in the treatment of metastatic cancers without causing cardiotoxicity and/or renal failure, as evidenced in the Example described in detail below.

A method of forming the nanoparticle system of the present invention is described in detail below. First, the biodegradable matrix can be dissolved in a water-based salt solution such as phosphate buffered saline (PBS) at a concentration ranging from about 1 milligrams/millimeter (mg/ml) to about 4 mg/ml, such as from about 1.5 mg/ml to about 3.5 mg/ml, such as from about 2 mg/ml to about 4 mg/ml to form a first solution. Then, the polysulphonated naphthylurea can be dissolved in a water-based salt solution such as PBS at a concentration ranging from about 0.08 mg/ml to about 0.7 mg/ml, such as from about 0.09 mg/ml to about 0.6 mg/ml, such as from about 0.1 mg/ml to about 0.5 mg/ml to form a second solution. Further, the water-based salt solution can have a pH ranging from about 6 to about 7.2, such as from about 6.4 to about 7.1, such as from about 6.8 to about 7. In addition, the chemotherapeutic agent can be dissolved in double-distilled water (dd$H_2O$) at a concentration ranging from about 0.25 mg/ml to about 2 mg/ml, such as from about 0.5 mg/ml to about 1.5 mg/ml, such as from about 0.75 mg/ml to about 1.25 mg/ml to form a third solution.

After the individual solutions containing the various components (e.g., the biodegradable matrix, polysulphonated naphthylurea, and chemotherapeutic agent) have been formed as described above, the second solution containing the polysulphonated naphthylurea and the third solution containing the chemotherapeutic agent can be combined to form a fourth solution, where the fourth solution can be slowly added to the first solution containing the biodegradable matrix. For instance, the fourth solution can be injected into the first solution at a rate ranging from about 0.05 milliliters/minute (ml/min) to about 0.4 ml/min, such as from about 0.075 ml/min to about 0.35 ml/min, such as from about 0.1 ml/min to about 0.3 ml/min via a microinjection pump with stirring at room temperature (about 20° C. to about 25° C.) for a time period ranging from about 10 minutes to about 1 hour, such as from about 20 minutes to about 40 minutes, such as from about 25 minutes to about 35 minutes to allow for the formation of nanoparticles. The resulting mixture containing the nanoparticles can then be centrifuged to remove any large aggregates, and the remaining nanoparticles can be lyophilized with 1% trehalose and stored at about 4° C. prior to use.

As shown in the following Example, the biodegradable matrix-polysulphonated naphthylurea-chemotherapeutic agent nanoparticles (e.g., the GCS-SM/DOX nanoparticles) of the present invention can effectively inhibit cancer cell migration and invasion, as well as angiogenesis associated with tumor cells. Furthermore, the GCS-SM/DOX nanoparticles of the present invention can significantly reduce the tumor burden and extended the lifetime of animals, while not inducing cardio and renal toxicities that are typically associated with DOX and SM, respectively. Moreover, since all of the components used in this system are biocompatible and easy for large-scale fabrication, the GCS-SM/DOX nanoparticle system is highly translatable for the treatment of metastatic breast cancer treatment. The GCS-SM/DOX nanoparticle system could also be used for the treatment of human sleeping sickness, onchocerciasis (river blindness), and autism.

The present invention may be better understood with reference to the following example.

EXAMPLE

1. Materials and Methods 1.1. Materials and Cell Lines

Glycol chitosan (GCS), suramin sodium salt (SM), doxorubicin (DOX), nuclei isolation kit (nuclei EZ prep), eosin Y, and BCA kit were purchased from Sigma (St. Louis, Mo.). Acidic fibroblast growth factor (aFGF) and basic fibroblast factor (bFGF) were purchased from Peprotech (NJ, USA). Luciferin was obtained from Merck Millipore. Gill's Hematoxylin No. 2 was purchased from VWR. Anti-CD31 antibody (ab28364) was purchased from Abcam. Dako envision kit was purchased from Dako (CA, USA).

Human breast cancer cell line MDA-MB-231 was obtained from the American Type Culture Collection (ATCC, Manassas, Va.) and cultured in Dulbecco's Modified Eagle Medium (DMEM) supplemented with 10% heat-inactivated fetal bovine serum (FBS), 100 U/mL of penicillin G sodium, and 100 µg/mL of streptomycin and a/b FGF at 10 ng/mL. Human umbilical vein endothelial cells (HUVECs) were obtained from Lonza (MD, USA) and incubated with complete EGM medium. Murine breast cancer cell line (E0771) were cultured in DMEM medium supplemented with 10% heat-inactivated fetal bovine serum (FBS), 100 U/mL of penicillin G sodium, and 100 µg/mL of streptomycin. All these cells were maintained at 37° C. in an atmosphere of 5% $CO_2$ and 95% air. MDA-MB-231/Luc-GFP cell, which stably expressing luciferase and green fluorescent protein, was a kind gift from Dr. Shirin Bonni (Medicine University of Calgary).

1.2. Preparation of DOX Loaded GCS-SM Nanoparticles (GCS-SM/DOX NPs)

GCS-SM/DOX nanoparticles (NPs) were prepared by the ionic gelation technique through the electrostatic effect between the negative charged sulfate groups of SM and positively charged amine groups of GCS. Typically, GCS was dissolved in phosphate-buffered saline (PBS, pH 7.0, 20 mM) to achieve the concentration of 2.8 mg/mL. SM was dissolved in the same buffer at the concentration of 0.5 mg/mL. DOX hydrochloride was dissolved in dd$H_2$O at the concentration of 1 mg/mL. One and a half milliliters of the SM solution prepared above was mixed with DOX solution first, and then injected slowly to 2.5 mL GCS solution at the speed of 0.2 mL/min with a microinjection pump (Harvard apparatus) with stirring (400 rpm) at room temperature. The mixture was stirred for 30 minutes to allow the formation of GCS-SM/DOX NPs. After that, the mixture was centrifuged at 1,000 relative centrifugal field (rcf) for 5 minutes to remove large aggregates. The resulting nanoparticles were lyophilized with 1% trehalose (w/w) and stored at 4° C. prior to use. Empty nanoparticles (GCS-SM) were prepared following the same protocol for GCS-SM/DOX NPs except no DOX was added. To investigate the effect of suramin concentration, pH of the buffer solution, volume of suramin, and DOX feeding ratio, GCS-SM/DOX NPs were prepared using the same method as described above by tuning one parameter while keeping all the other parameters constant or unchanged.

The size and surface charge (ξ-potential) of the nanoparticles were measured using a Zetasizer Nano-ZS (Malvern, UK) at pH 7.4. The morphology of the GCS-SM/DOX NPs was observed by transmission electron microscopy (Hitachi H-800 TEM) using a formvar/carbon coated Copper Grids (Electron Microscopy Science). The original particle suspension was dropped on a grid, washed with dd$H_2$O (3×) to remove the remaining salt, and dried using filter paper. DOX and SM concentrations were determined by UV-Vis spectrometer (Beckman, DU650) at 480 nanometers (nm) and 312 nm, respectively.

1.3. Encapsulation Efficiency of GCS-SM/DOX NPs

To evaluate the encapsulation of DOX in the GCS-SM/DOX NPs, DOX was loaded into the nanoparticles at different feeding ratios (e.g., 1.3%, 3.6%, and 9.0% weight ratio of DOX:GCS). The un-encapsulated DOX was separated from the NP suspension using a Millipore centrifugal device of 30K MWCO at the speed of 3,000 rcf for 30 minutes. The concentration of free DOX was determined by a fluorescent plate reader.

1.4. Release Kinetics of GCS-SM/DOX NPs

Two milliliters of GCS-SM/DOX NPs were loaded in dialysis bags (MWCO: 6-8 KDa, Spectrum laboratories) and were put into 25 mL of PBS (pH 7.4, 100 mM) at 37° C. under continuous stirring. At predesigned time points, 1 mL of media was withdrawn. Concentrations of SM or DOX were determined by UV-Vis spectrometer (Beckman, DU650) at 312 nm and 480 nm, respectively. All experiments were carried out in triplicate independently.

1.5. Colloid Stability of GCS-SM/DOX NPs

GCS-SM/DOX NPs were suspended in PBS 7.4 supplemented with different amounts of fetal bovine serum (FBS), ranging from 10% to 30%, with the final concentration of SM at 100 µM at 37° C. The size of the nanoparticles was measured at pre-determined time points with dynamic light scattering (DLS).

1.6. Quantification of Cellular Uptake of GCS-SM/DOX NPs

Cellular uptake of GCS-SM/DOX NPs was quantified by flow cytometry and confocal microscopy. The intracellular distribution of the DOX was measured by cell fraction assay. MDA-MB-231 cells were seeded in 12 well plates at 200,000 cells/well and treated with DOX or GCS-SM/DOX NPs at the DOX concentration of 1 µM for 3 hours. Afterwards, cells were washed 3 times with cold PBS to remove unbound DOX or nanoparticles. Cells were collected, fixed in 4% formaldehyde, and analyzed by FACS (BD Accuri C6, BD Biosciences).

To further investigate the uptake behaviors of nanoparticles, confocal microscopy was employed. MDA-MB-231 cells were seeded in petri dishes and treated with DOX or GCS-SM/DOX NPs at a DOX concentration of 1 µg/mL. After 3 hours of co-incubation, cells were washed 3 times and images were taken with a Zeiss 710 LM confocal microscope.

GCS-SM/DOX NPs were incubated with MDA-MB-231 cells at 37° C. for 1 hour. Cells were washed 3 times, then collected by scraping. Cells were subjected to subcellular fractionation after the treatment. In brief, the cells were re-suspended in a harvest buffer (0.01 M HEPES, 50 mM NaCl pH 7.9, containing 0.5 M sucrose, 0.5% triton X-100) and pelleted at 1,000 rpm for 10 minutes. The supernatant was collected as a cytoplasmic protein fraction. The pellets were washed once with buffer (0.01 M HEPES, 10 mM KCl, 0.1 mM EDTA, 0.1 mM EGTA) and followed by further incubating with another buffer (0.01 M HEPES, 0.5 M NaCl, 0.1 mM EDTA, 0.1 mM EGTA, 0.1% NP-40) for 15 minutes on ice. The nuclear fraction was further sonicated (3× for 10 seconds, separated by 1 minute). The nuclear fraction was collected by pelleting the suspension through centrifugation at 400 rcf for 10 minutes. Cytosolic and nuclear fractions obtained from subcellular fractionation of MDA-MB-231 cells were further cleared by centrifugation at 10,000 rcf for 15 minutes at 4° C. DOX uptake amount was quantified by the fluorescent intensity at the excitation at 485 nm with the emission at 585 nm. The protein concentration of cytosol and nuclear fraction were quantified by BCA assay kit.

1.7. Wound Healing Assay

The migration of breast cancer cells was evaluated with a wound healing assay. Living videos of cell migration in a 24-well plate were acquired with a Zeiss 710 LM confocal microscope. MDA-MB-231 cells were pretreated with a/b FGF for 24 hours. After that, a wound was created by scraping the cell monolayer in a straight line with a p200 tip, and cell debris was removed by washing with PBS three times. Cells were incubated with different treatments and allowed to grow in a 37° C. chamber with 5% $CO_2$ for 24 hours. Videos were taken using a confocal microscope with a transmittance channel continuously at 10× magnification.

1.8. Cell Invasion Assay

BD cell culture inserts with a pore size of 8 μm (BD, Biosciences) were pre-coated with 100 μL of Matrigel at the concentration of 0.2 mg/mL (dilution from BD Matrigel stock 10 mg/mL with coating buffer). MDA-MB-231 cells were seeded at a density of 70,000 cells per 50 μL in the inserts in an FBS-free DMEM medium. SM or GCS-SM NPs was then added to the inserts together with 50 μL serum free medium. Each lower chamber was supplied with 1.2 mL 10% FBS containing medium supplemented with different treatments that were the same as each respective top chamber. After 16 hours of incubation, the inserts were washed with PBS and fixed with methanol. Subsequently, cells were stained with hematoxylin and washed twice with PBS. The membrane in each of the inserts was then cut and mounted onto a coverslip, and the cell number was counted with a light microscope under 10× magnification. Each well was imaged at 5 different fields, and the invasion rate was expressed by the average number of cells per microscopic field.

1.9. Endothelial Tube Formation Assay

Human umbilical vein endothelial cells (HUVECs) were cultured and maintained in a complete EGM Medium. Cells were stained with Celltracker Deep red (1 μM) for 30 minutes prior to the experiment. One hundred and fifty microliters (μL) of Geltrex® (Thermofisher) was added to each well in a 24-well plate and allowed to be polymerized for 30 minutes at 37° C. HUVEC cells were seeded in each well at a density of 2×10$^5$ cells/mL. SM, GCS, and GCS-SM NPs at concentrations of 10 μM and 20 μM were mixed with cells prior to seeding in the coated gel layer. The tube formation was photographed at 6 hours and 20 hours with an inverted phase contrast microscope (Canon Powershot A640) in a randomly selected field under 10× magnification, and the number of formed tubes and length of the tubes were quantified manually by Image J. Fluorescent images of cells were photographed by Zeiss 710 LM confocal microscope under 10× magnification.

1.10. Cell Viability Assay

The anticancer activities of the combination of DOX and SM were investigated with an MTT colorimetric assay. Cells with or without a/b FGF treatment were seeded in 96-well plates at an initial density of 20,000 cells/well. After 24 hours of incubation, the medium was replaced with 150 μL of fresh medium containing different treatments, including DOX, SM, and the combination of DOX and SM, and continued to be incubated for an additional 24 hours or 48 hours. Afterwards, the media were replaced with 100 μL fresh media containing 1 mg/mL MTT reagent and incubated for another 4 hours. The formed MTT crystals were dissolved with a stop solution and the final optical density of the medium was measured using a microplate reader (ELX808, Bio-Tech Instrument, Inc.) at λ=595 nm. A combination index (CI) analysis based on the Chou-Talalay method was performed using CalcuSyn software.

1.11. In Vivo Experiment

All animal experiments were conducted in accordance with NIH regulations and approved by the Institutional Animal Care and Use Committee of the University of South Carolina. Female athymic mice at the age of 6 to 8 weeks (nu/nu) were obtained from Jackson laboratory. MDA-MB-231/Luc-GFP cells were implanted by tail vein injection (2×10$^6$ cells in 100 μL PBS). Mice were then randomly divided into 5 groups and received the following treatments: 1) saline only; 2) SM at the dose of 3.5 mg/kg once per week; 3) free SM and DOX at the dose of 3.5 mg/kg of SM and 0.5 mg/kg of DOX once per week; 4) GCS-SM NPs at the dose of 3.5 mg/kg of SM once per week; 5) GCS-SM/DOX NPs at the dose of 3.5 mg/kg of SM and 0.5 mg/kg of DOX (molar ratio of SM to DOX is 17:1) once per week. The whole treating procedure lasted for two months and the progression of tumors was monitored every week by luminescence with an IVIS Lumia system after i.v. injection of luciferin (30 mg/mL, 50 μL). Bodyweights of the mice were recorded at the same time. At the endpoint of each mouse, organs were isolated and collected. The weights of the lungs were recorded. Fluorescent images of the lungs were also captured. The collected organs were fixed in 10% neutralized formalin solution and embedded in paraffin.

1.12. Immunohistochemistry and Histological Analysis

Tissue sections of 5 μm thickness were obtained from the formalin fixed, paraffin embedded tissue blocks with a microtome. The standard hematoxylin and eosin staining was performed in the lung, liver and kidney tissue sections of each group. To study the tumor neovasculature, CD31 IHC was applied to identify the intra-tumor blood vessel distribution. The section was deparaffinized and treated for 30 minutes with 0.5 M Tris buffer (pH 10) at 95° C. for antigen retrieval. Sections were blocked in 5% goat serum for 20 min at room temperature. The sections were blocked with peroxidase block for 5 minutes and incubated with a primary antibody (rabbit polyclonal anti-CD31 antibody) diluted with 1% BSA (1:50) for 1 hour at room temperature, followed by the staining with peroxidase labelled polymer for 30 minutes at room temperature. The sections were then developed with the substrate-DAB for 5 minutes at room temperature and counterstained with Gill's Hematoxylin for 10 seconds. The slides were mounted with ProLong® Gold Antifade Mountant and imaged at 40× magnification with a microscope.

1.13. Statistical Analysis

Statistical Analysis was performed via the one-way ANOVA test using the software SigmaPlot 12.0. (Systat Software Inc., San Jose, Calif., USA). The values of *$P<0.05$ and #$P<0.01$ were determined as statistically significant. Data was expressed as means±standard deviation (SD).

2. Results 2.1. DOX Encapsulated GCS-SM (GCS-SM/DOX) NP Preparation

It has been reported that chitosan can form hydrogels with tripolyphosphate (TPP). Many factors can affect the size of nanoparticles, especially the TPP to chitosan ratio, pH of the buffer and the ionic strength of the dissolution medium. A few reports have shown that chitosan is able to form a hydrogel with sodium lauryl sulfate. Inspired by this nanoparticle fabrication technology, the concept of creating GCS-SM NPs through a gelation process between the sulfate groups on SM and amine groups on GCS, where SM acted as an anionic compartment and GCS acted as a cationic counterpart, was tested. Moreover, as the anionic and cationic compounds account for significant fractions of this delivery system, it was hypothesized that the loading capacity of a therapeutic agent could be greatly improved if one of the compounds coincidentally was an active pharmaceutical ingredient.

In order to examine the effect of SM concentration on nanoparticle size, the GCS concentration was fixed at 2.8 mg/mL in PBS buffer (pH 7.4). With the SM concentration declining from 25% to 5% (w/w, SM/GCS), the hydrodynamic size of nanoparticle was slightly increased from 220 nm to 277 nm along with the increased PDI (polydispersity index). The relationships among particle size, SM content in the final formulation, pH of the fabrication buffer, as well as the concentration of SM are shown in FIGS. 2A, 2B, 2C, and 2D. When the pH of the fabrication buffer varied from 6 to 7.4, the size of nanoparticles changed from 210 nm to 298 nm accordingly. It was revealed that too low or too high of a pH inhibited the formation of the nanoparticles. Without intending to be limited by any particular theory, the present inventor believes this is due to the fact that too high or too low pH can prevent the ionization of one component of the system. Interestingly, within the range of 0.1 to 0.5 mg/mL, the concentration of SM did not have significant effect on the size of the nanoparticle. However, when the concentration of SM reached 1 mg/mL, the resulting nanoparticles had a final size over 600 nm with a PDI of 0.25. See FIG. 2C. In addition, it was found that the loading of DOX had little impact on the hydrodynamic size of the nanoparticle. Therefore, the payload amount could be tuned without significantly affecting the size of the nanoparticles.

2.2. Characterization of GCS-SM/DOX NP

Figure 3A:
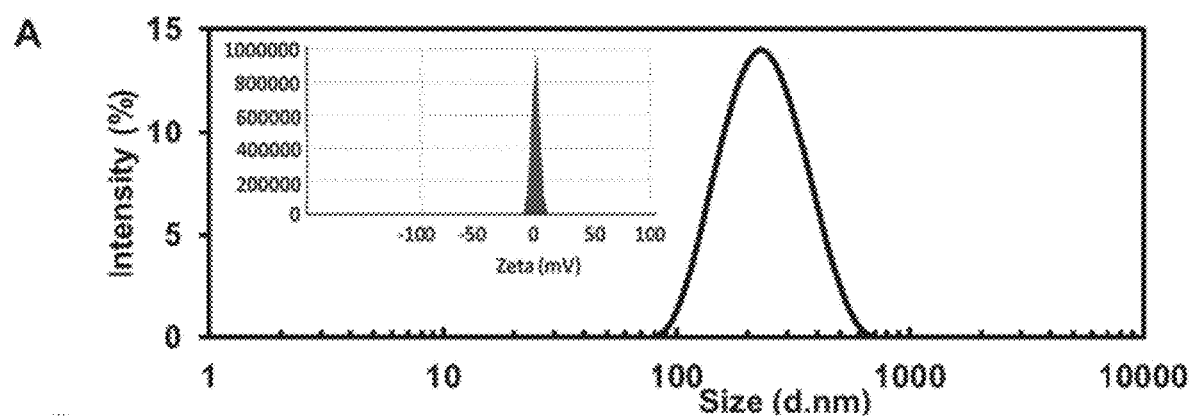
FIG. 3A illustrates the hydrodynamic size distribution and surface charge of the glycol chitosan (GCS)-SM/DOX nanoparticles of the present invention.
Figure 3B:
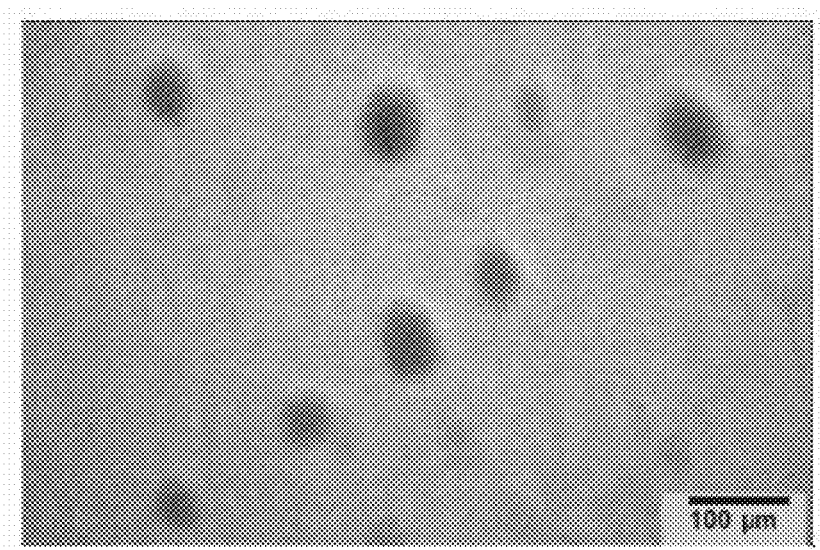
FIG. 3B is a transmission electron microscopy image of GCS-SM/DOX nanoparticles at 100,000× magnification, where the scale bar is 100 nanometers.

Based on the above investigation, nanoparticles with a SM to chitosan ratio of 16% (w/w) in 20 mM PBS buffer (pH 7.0) at a SM concentration of 0.5 mg/mL were fabricated. Dynamic light scattering (DLS) revealed that the resulting nanoparticles had a hydrodynamic size of 186.1 nm coupled with a slightly positive surface charge (+1.2 mV) as shown in FIG. 3A. Transmission electron microscopy revealed that these nanoparticles were in spherical shape with the average size of 49.0 nm as shown in FIG. 3B. The size difference between DLS and TEM results may be due to: (1) DLS measures that the hydrodynamic diameter of the nanoparticles suspended in PBS while TEM measures the size of dried nanoparticles; and (2) especially in the case of GCS-based nanoparticles, the high density of the more hydrophilic ethylene group grafted on the backbone of chitosan further increases the interaction with the aqueous medium, which consequently extends the thickness of the water layer associated with the particle. The free DOX in the final nanoparticle suspension was less than 3% regardless the feeding ratio of DOX to GCS in the tested range, which suggests that GCS-SM is a good carrier system for DOX.

Figure 3C:
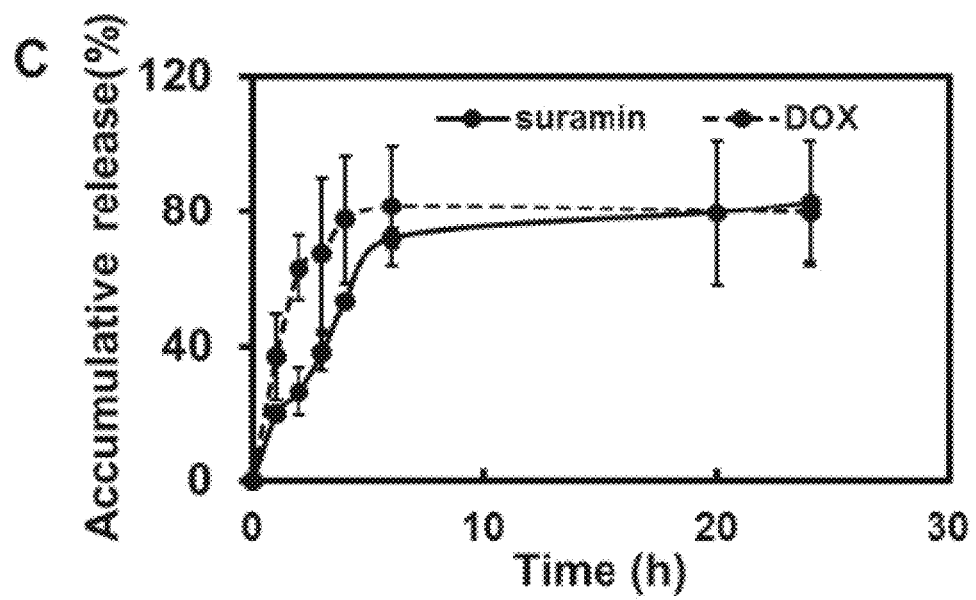
FIG. 3C is a graph showing the in vitro release of suramin and doxorubicin in phosphate buffered saline (PBS).
Figure 3D:
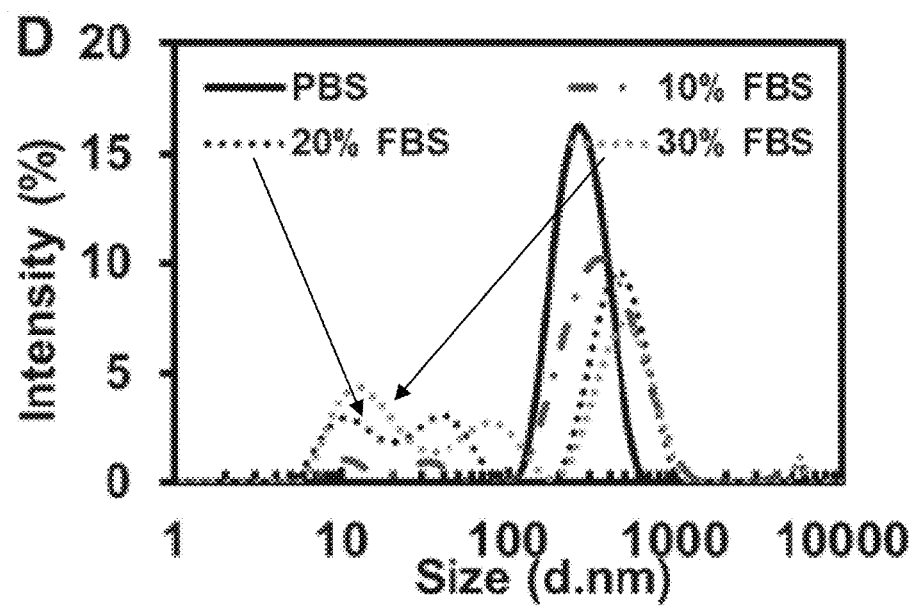
FIG. 3D is a graph illustrating the hydrodynamic size of GCS-SM nanoparticles when co-incubated with fetal bovine serum (FBS) at various concentrations ranging from 0% FBS to 30% FBS.
Figure 3E:
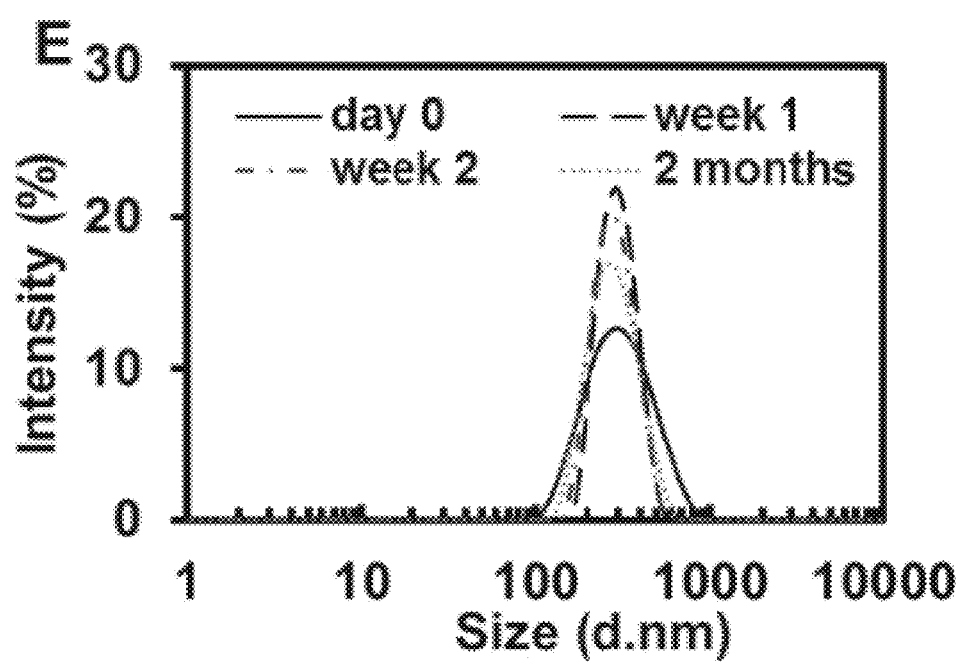
FIG. 3E is a graph illustrating the long-term stability of GCS-SM nanoparticles in PBS.

FIG. 3C shows the release behaviors of SM and DOX from the nanoparticles. It was revealed that DOX and SM shared a similar release pattern, where after 8 hours of incubation in PBS at a pH of 7.4, both the DOX and SM had reached a plateau of around 80%. The simultaneous release pattern for DOX and SM ascertained the optimized ratio between the two drugs remained unchanged from the point of the preparation to their active site. Since the complex was slightly positive, there was concern about the colloid stability of the nanoparticles. The stability of the nanoparticles was evaluated through the long-term incubation of NPs in PBS and the short-term incubation of NPs supplemented with FBS. FIG. 3D shows that these NPs were stable and did not aggregate in 10% serum-containing media. FIG. 3E shows that the NPs were very stable in a PBS environment, as evidenced by no size increase after two months incubation at 37° C.

2.3. GCS-SM NP Inhibitory Effect on Cell Migration and Invasion

Figure 4A:
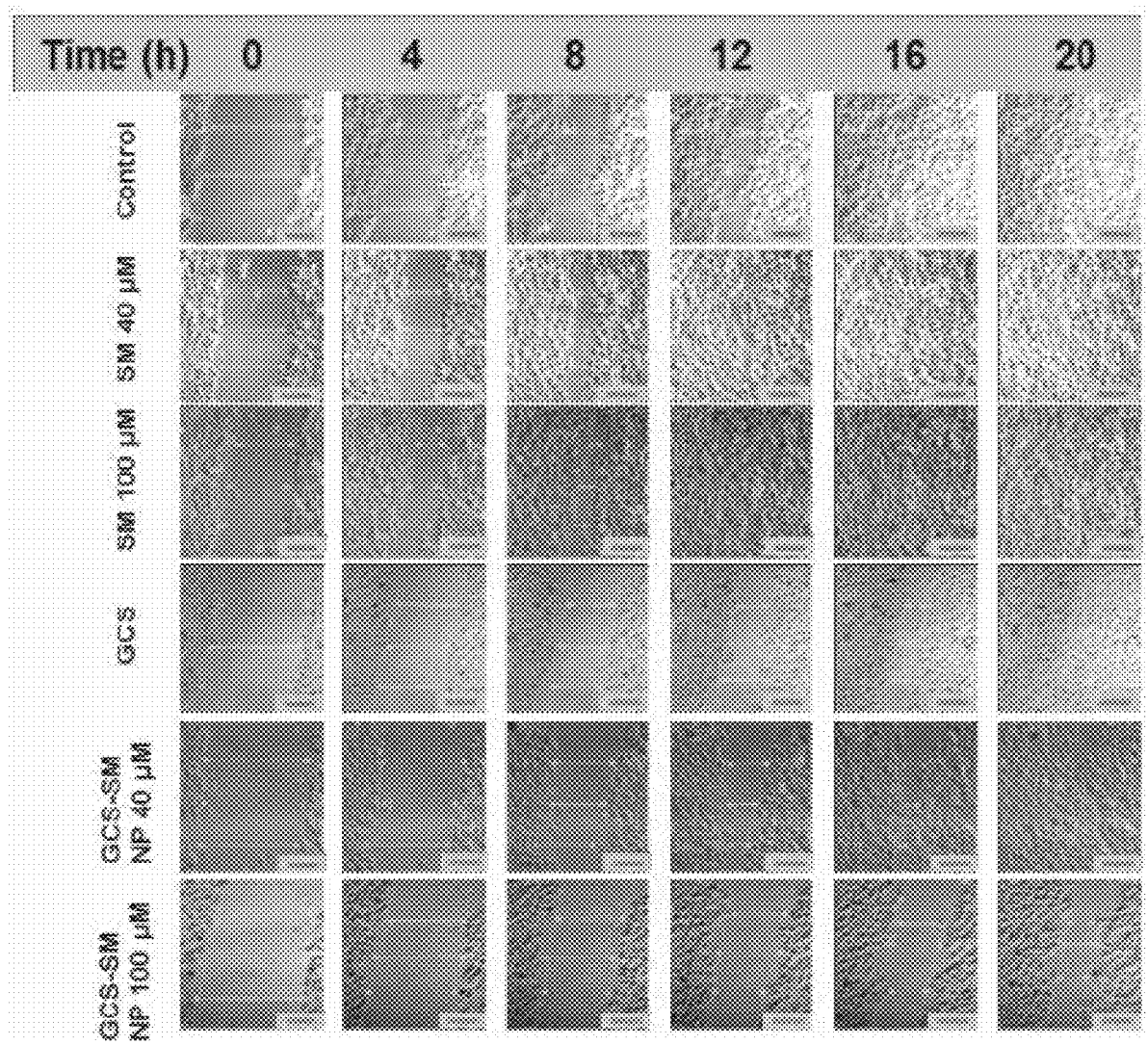
FIG. 4A shows images that detail the migration of MDA-MB-231 cells after being treated with SM, GCS, or GCS-SM nanoparticles at various concentrations compared to a control at various concentrations at 0, 4, 8, 12, 16 and 20 hours, where the scale bars are 150 micrometers.
Figure 4B:
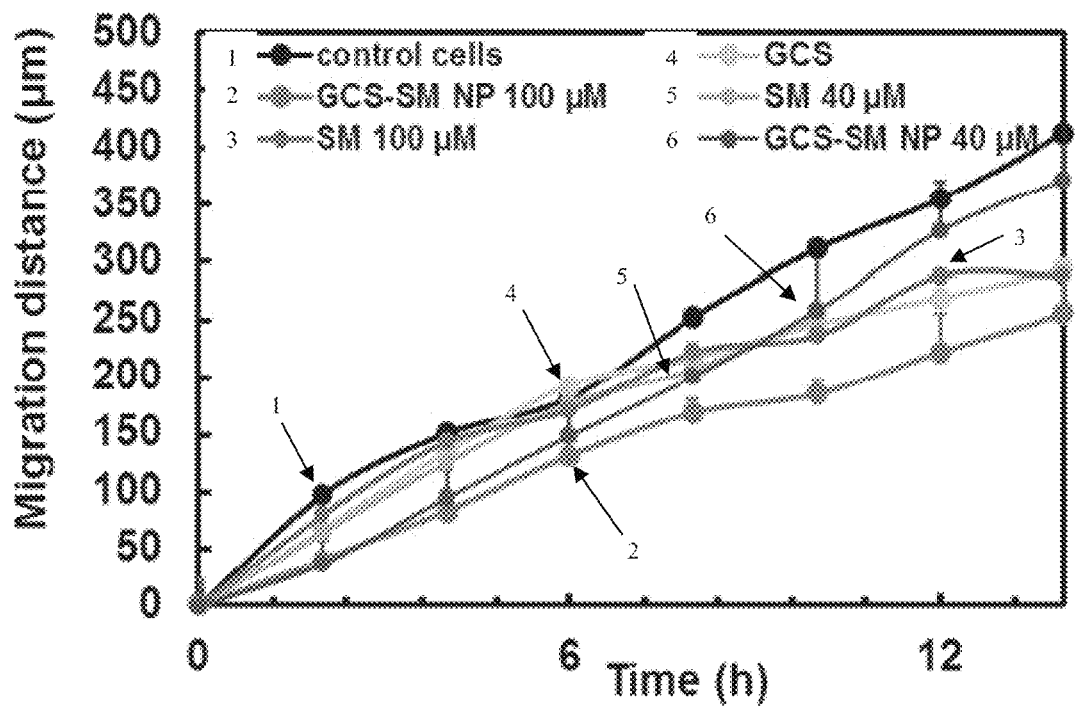
FIG. 4B is a graph illustrating the migration distance of cells treated with SM, GCS, or GCS-SM at various concentrations compared to a control.
Figure 4C:
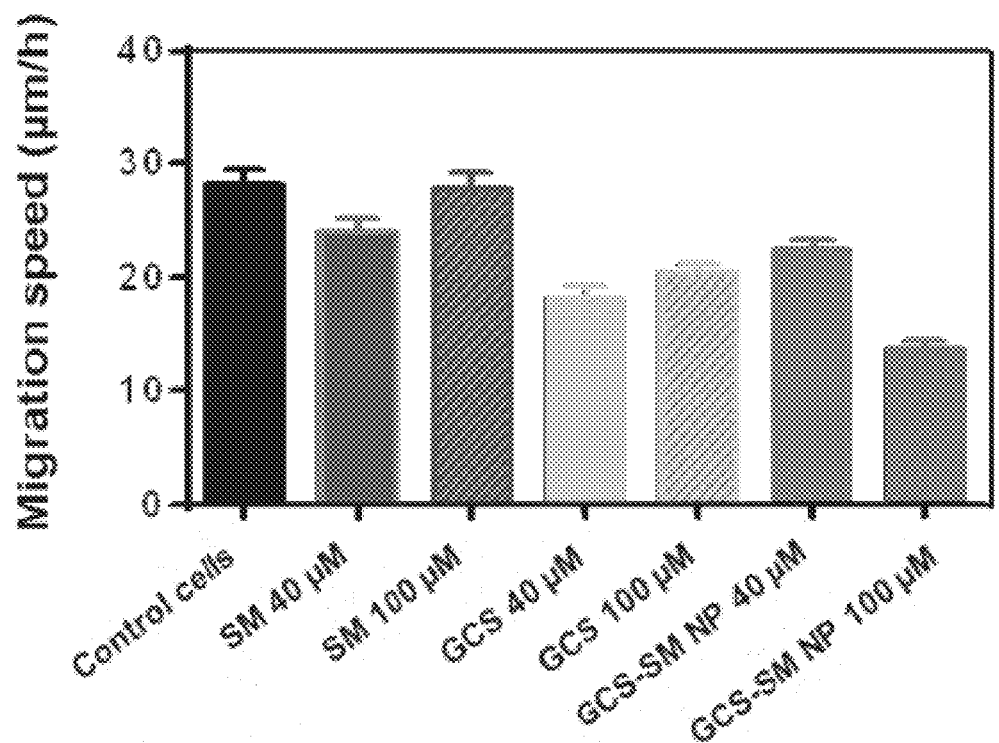
FIG. 4C is a graph illustrating the migration speed of cells treated with SM, GCS, or GCS-SM at various concentrations compared to a control.
Figure 4D:
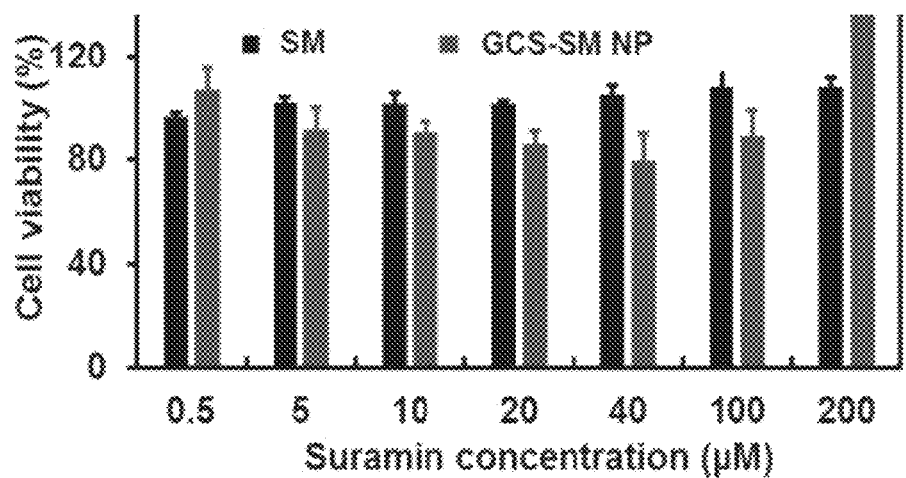
FIG. 4D is a graph illustrating the cytotoxicity of SM, GCS, or GCS-SM at various concentrations compared to a control after 24 hours.

To investigate the effect of SM or SM loaded nanoparticles on breast cancer cell migration and invasion, a wound healing assay and a Transwell invasion assay were carried out, respectively. Both the MDA-MB-231 human breast cancer cell line and the E0771 murine breast cancer cell line were tested in these assays. In the wound healing assay, the effects of different treatments on cell migration were analyzed by live cell imaging, as shown in FIGS. 4A-4F. The average speed for cell migration was calculated by dividing the wound distance by the time consumed to heal the wound. FIGS. 4A and 4B showed that SM only slightly inhibited cell migration, while its inhibitory effect was significantly enhanced in the GCS-SM nanoparticle form. The control group had an average migration speed of 28.2 µm/h, as shown in FIG. 4C. Interestingly, GCS itself also showed a noticeable inhibition effect on cell migration with an average speed of 18.2 µm/h. Without intending to be limited by any particular theory, the cause of the inhibition may be because GCS up-regulates E-cadherin and down-regulates slug and twist 1 expression. To investigate whether the inhibitory effect of SM and SM nanoparticle on cell migration was due to its cytotoxic effect, a cell viability assay was performed. It was found that neither SM nor GCS-SM NP inhibited cell proliferation at concentrations up to 200 µM within 24 h of treatment, as shown in FIG. 4D, which indicates that the inhibition of cell migration could not be attributed to cytotoxic effects.

Figure 4E:
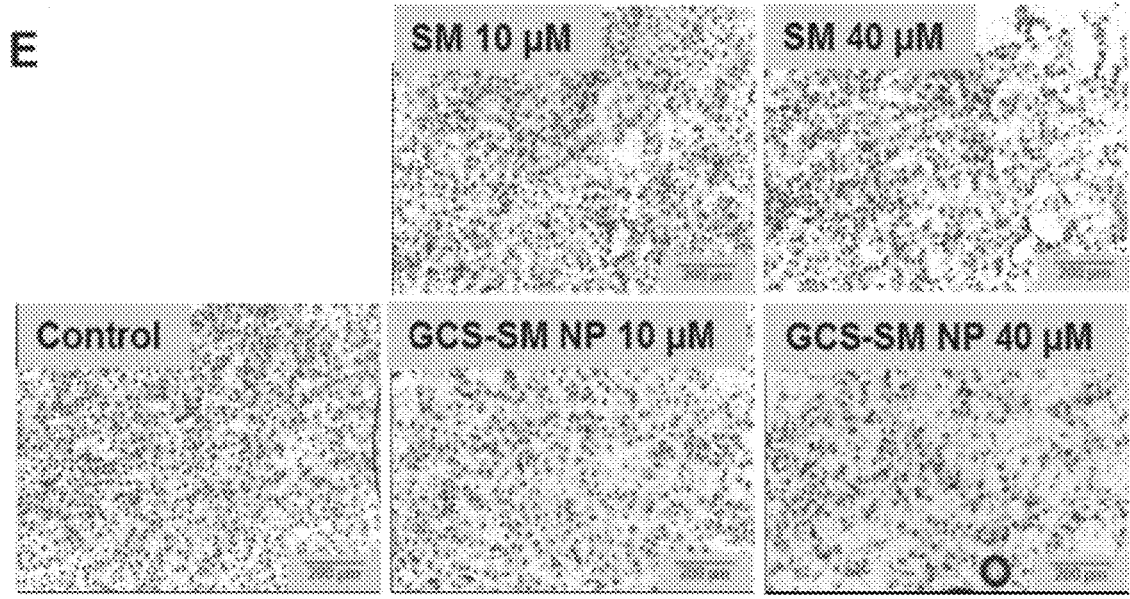
FIG. 4E shows images that detail the invasion of MDA-MB-231 cells that have been treated with the SM or GCS-SM nanoparticles compared to a control, where the scale bars are 200 micrometers.
Figure 4F:
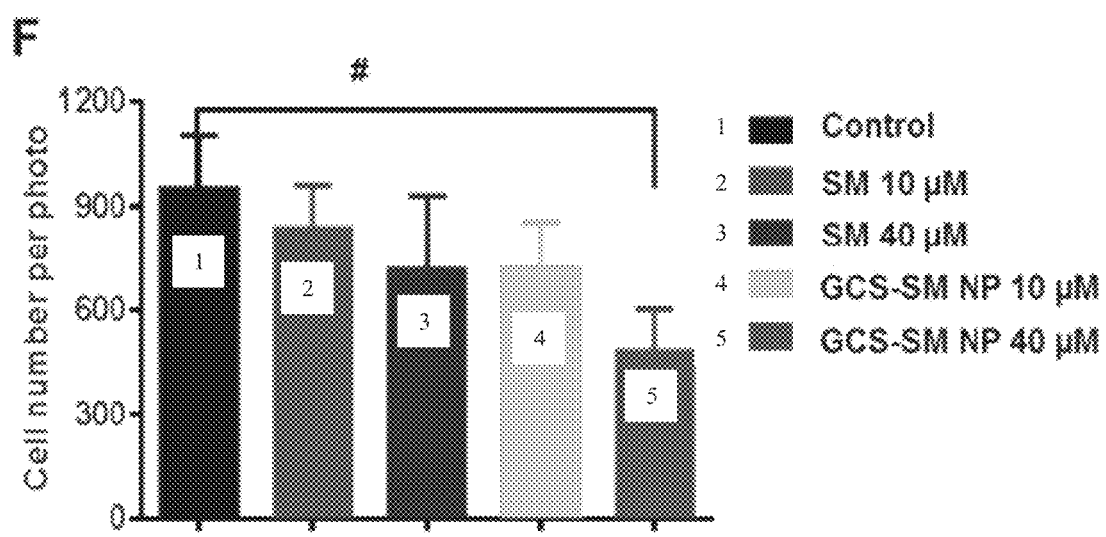
FIG. 4F is a graph illustrating the number of MDA-MB-231 cells associated with each of the images in FIG. 4E 16 hours after the cells were treated with the nanoparticles.

To investigate the inhibitory effect of SM and GCS-SM NPs on cell invasion, a Transwell invasion assay was carried out with MDA-MB-231 and E0771 cells. FIGS. 4E and 4F show that the number of invaded MDA-MB-231 cells in each view area was significantly decreased from 952 in the control group to 718 in the group treated with 40 µM SM. GCS-SM NPs treatment further decreased the number to 50% of the control. GCS-SM NP did not inhibit cell proliferation up to 25 µM after 24 hours of incubation, as evidenced by the MTT assay. However, GCS-SM NPs (10 µM) exhibited an enhanced inhibitory effect on cell invasion as compared with free SM. Thus, it was proven that SM or GCS-SM NPs inhibited both cell migration and invasion at a dose that does not induce cytotoxicity.

Figure 5A:
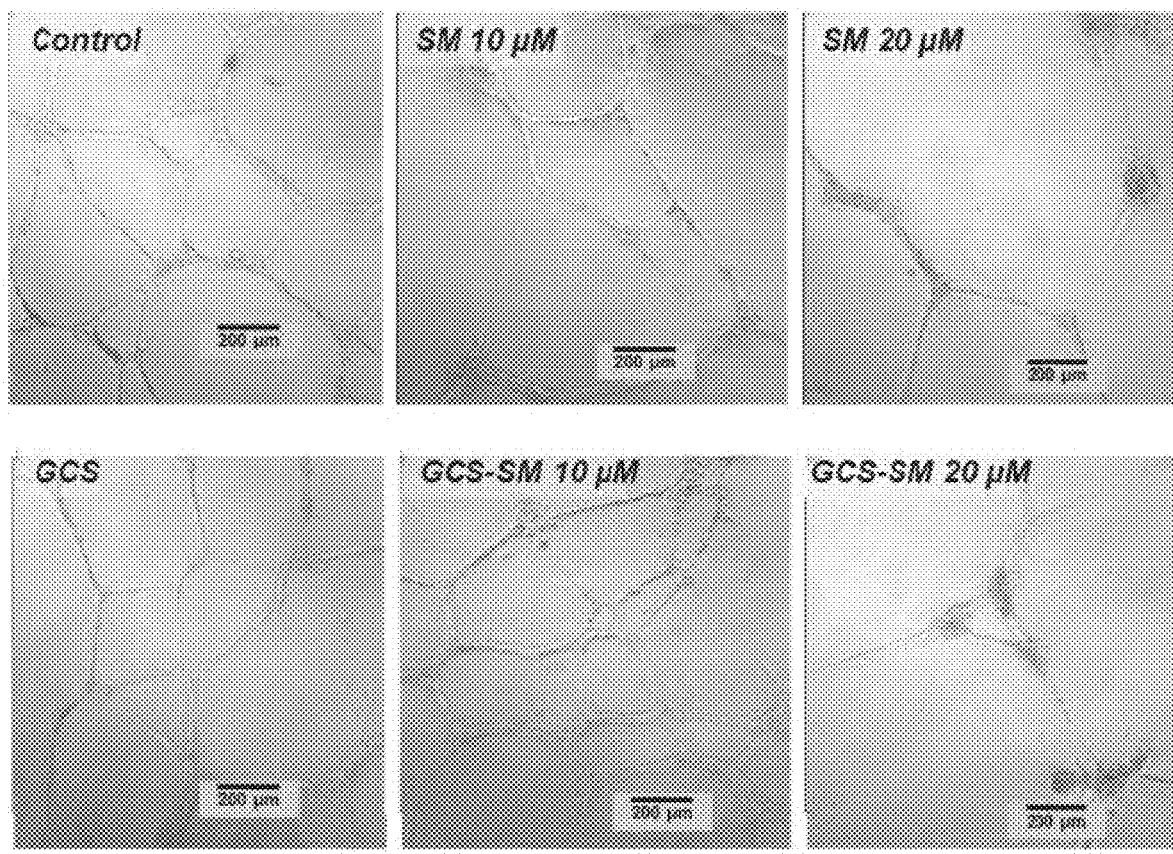
FIG. 5A shows images of human umbilical vein endothelial cells (HUVEC) tubes formed after treatment with SM, GCS, and GCS-SM nanoparticles compared to a control at 10× magnification, where the scale bars are 200 micrometers.
Figure 5B:
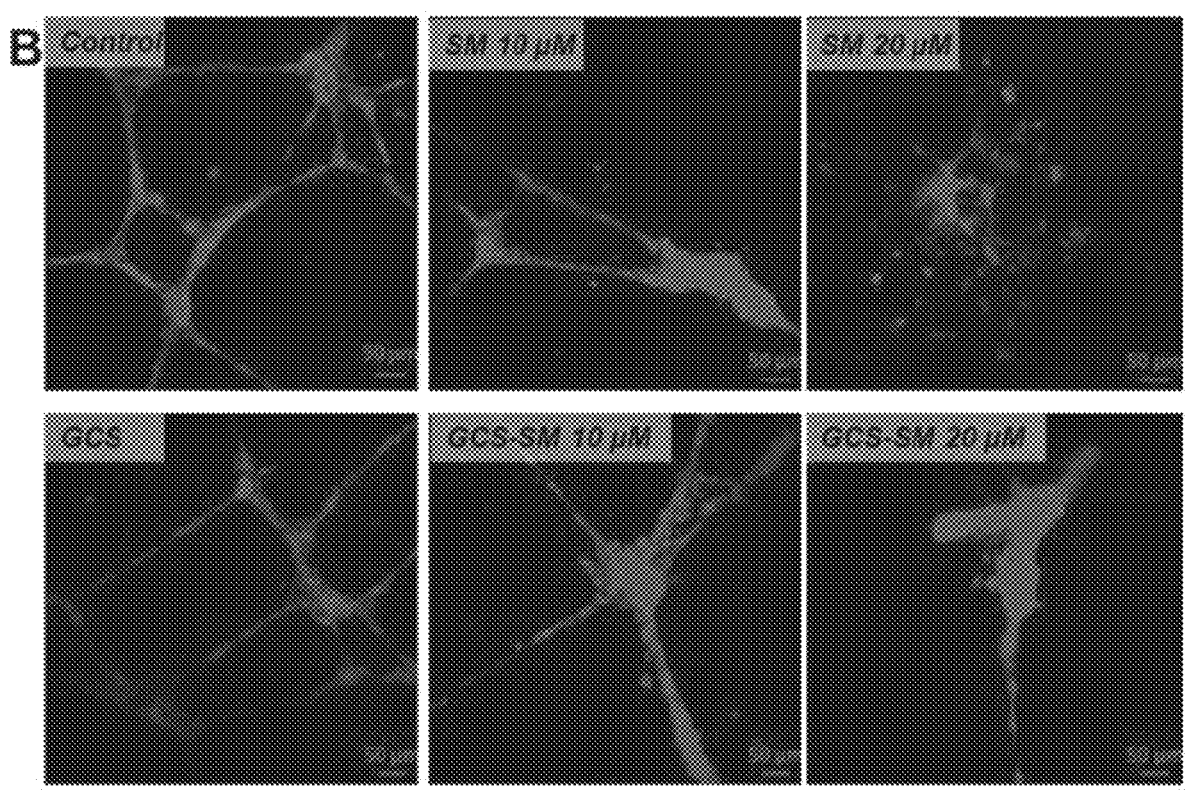
FIG. 5B shows confocal microscopy images of human umbilical vein endothelial cells (HUVEC) tubes formed after treatment with SM, GCS, and GCS-SM nanoparticles compared to a control at 100× magnification, where the scale bars are 50 micrometers.
Figure 5C:
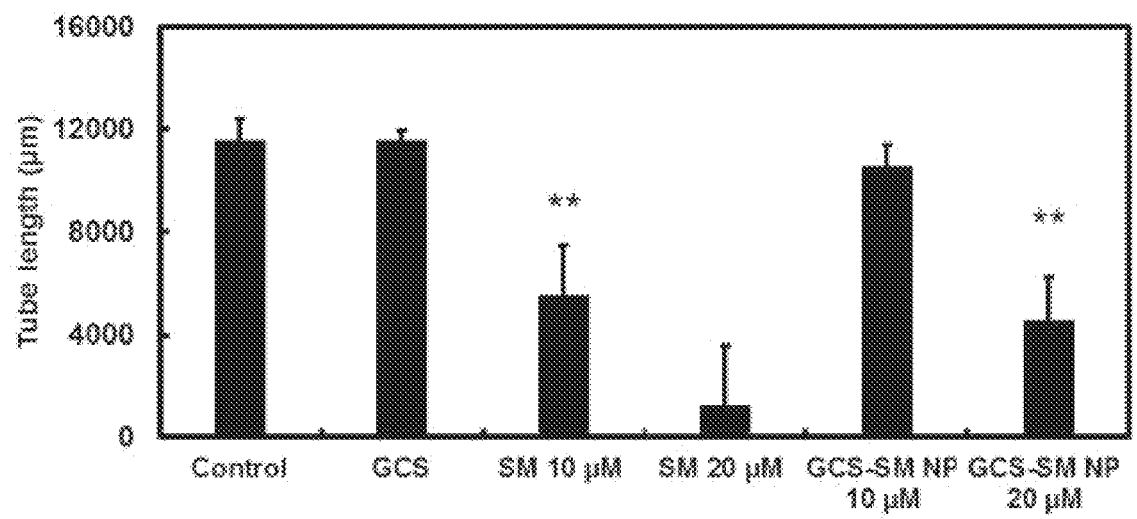
FIG. 5C is a graph illustrating endothelial cell tube formation expressed as length of tubes/field.
Figure 5D:
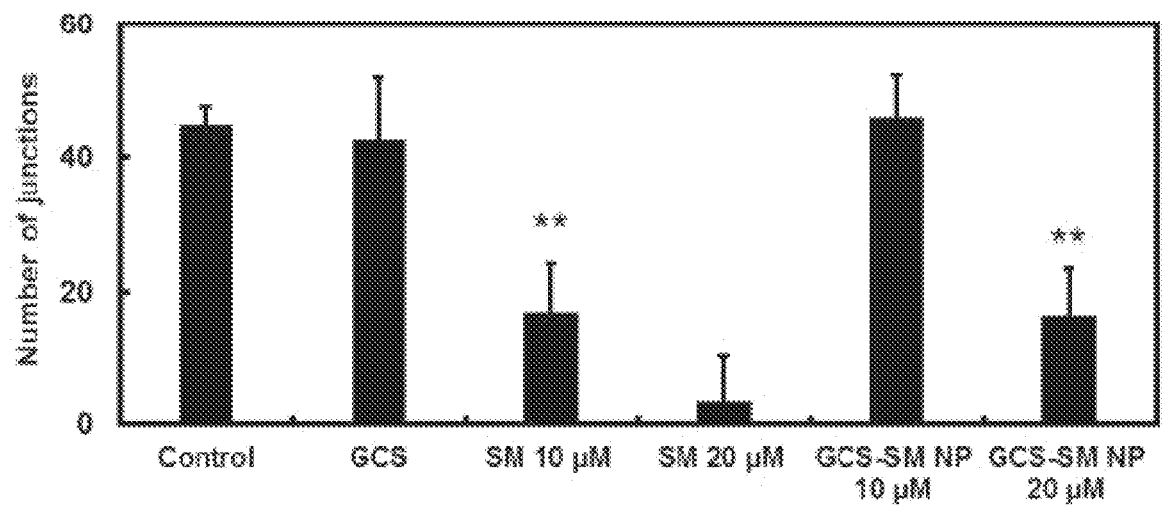
FIG. 5D is a graph illustrating endothelial cell tube formation expressed as number of tubes/fields.

To investigate the anti-angiogenesis effect of SM, an in vitro tube formation assay was employed. When HUVEC cells were seeded on the top of Geltrex®, elongated and robust tube-like structures were formed. The effects of GCS-SM NPs on the ability of HUVECs to form tube-like structure were evaluated by measuring the length and the number of formed tubes. FIGS. 5A and 5B show that the tube formation ability of HUVECs was significantly inhibited by the treatment of SM or GCS-SM NPs. At a concentration of 20 GCS-SM NPs were able to inhibit tube formation in aspects of both tube number and tube length by 50%. Free SM also showed an inhibitory effect on tube formation, where it is speculated that it is partially due to the interaction of sulfate groups in SM and the Geltrex® layer. See FIGS. 5C and 5D.

2.4. Cellular Uptake and Subcellular Distribution of GCS-SM/DOX NPs

Figure 6A:
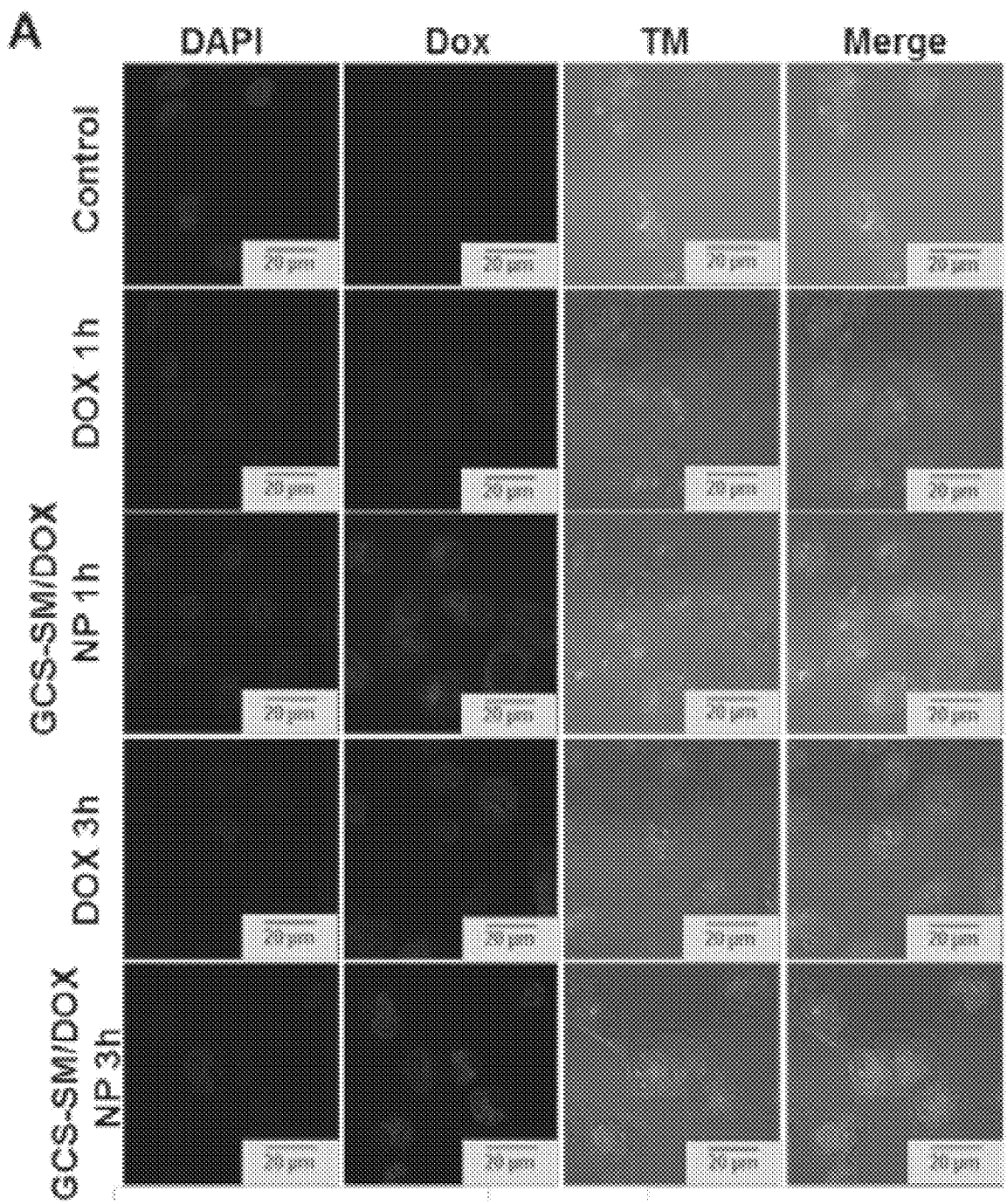
FIG. 6A shows confocal microscopy images of the uptake of doxorubicin (DOX) or GCS-M/DOX nanoparticles in MDA-MB-231 cells up to about 3 hours, where the scale bars are 20 micrometers.
Figure 6B:
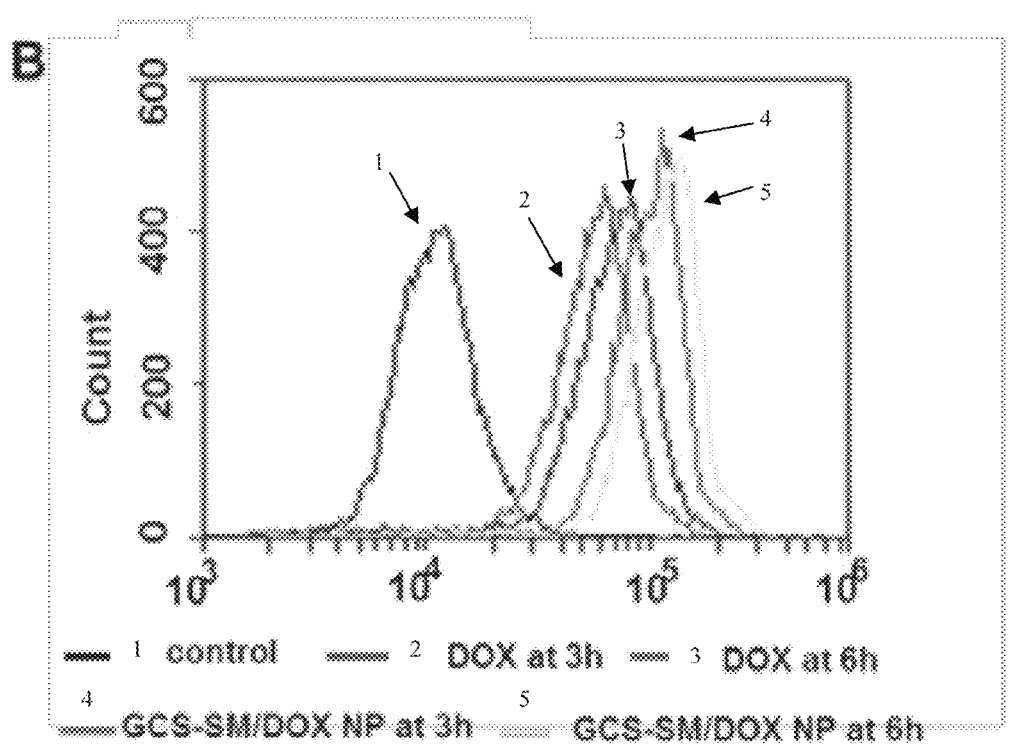
FIG. 6B is a graph illustrating the flow cytometry (FACS) spectra of MDA-MB-231 cells treated with free DOX or GCS-SM/DOX nanoparticles for 3 hours or 6 hours.

To measure the uptake efficiency of GCS-SM/DOX NPs in vitro, MDA-MB-231 cells pretreated with a/b FGF were incubated with free DOX and GCS-SM/DOX NPs. After 1, 3, and 6 hours of incubation, cells were analyzed by flow cytometry (FACS) and confocal microscopy. FIG. 6A shows that free DOX entered cells much more slowly than GCS-SM/DOX NPs. After 1 hour of treatment, NP treated cells exhibited a much stronger red fluorescence signal inside the cell than those in the free DOX treatment group. It was revealed that almost all of the DOX that was delivered by NPs was in the nuclei, while much of the DOX from the free DOX treatment still stayed in the cytosol after 3 hours of treatment. Using FACS, the cellular uptake behaviors of free DOX or GCS-SM/DOX NPs at 3 hours and 6 hours with the presence of a/b FGF was compared, as shown in FIG. 6B. In the presence of a/b FGF, GCS-SM/DOX NP treated cells showed much better DOX uptake compared to free DOX. The fact that the presence of a/b FGF results in differences in DOX uptake between GCS-SM/DOX NPs and free DOX may be because FGF might induce chemo-resistance, while SM could sensitize the drug resistant cells.

Figure 6C:
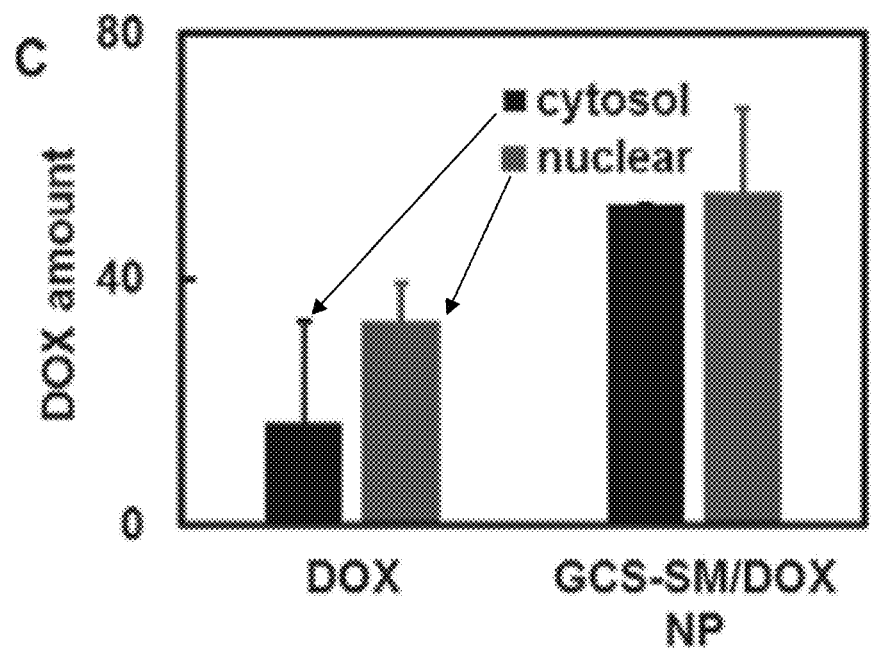
FIG. 6C is a graph illustrating the DOX distribution in the cytosol and nuclei after treating MDA-MB-231 cells with DOX or GCS-SM/DOX nanoparticles for 1 hour.

Nuclear localization of DOX has always played an important role for its potency in killing cancer cells. A higher localization in nuclei has been closely related to its DNA binding capacity. After treating cells with a/b FGF, FIG. 6C shows that the 1 hour DOX uptake in the treatment group of GCS-SM/DOX NP was significantly enhanced in the nuclear subcellular fraction, suggesting a higher anti-cancer efficacy against MDA-MB-231 cells.

2.5. SM and DOX have Synergistic Growth Inhibitory Effect on MDA-MB-231 Cells

SM showed biphasic effects on the proliferation of cancer cells. On one hand, as a non-specific growth factor inhibitor, it inhibits angiogenesis of cancer cells. On the other hand, high concentrations of SM kill cancer cells directly. Although it has been reported that SM kills cancer cells in a dose-dependent and time-dependent manner, the cell killing mechanism is still not fully understood.

Figure 6D:
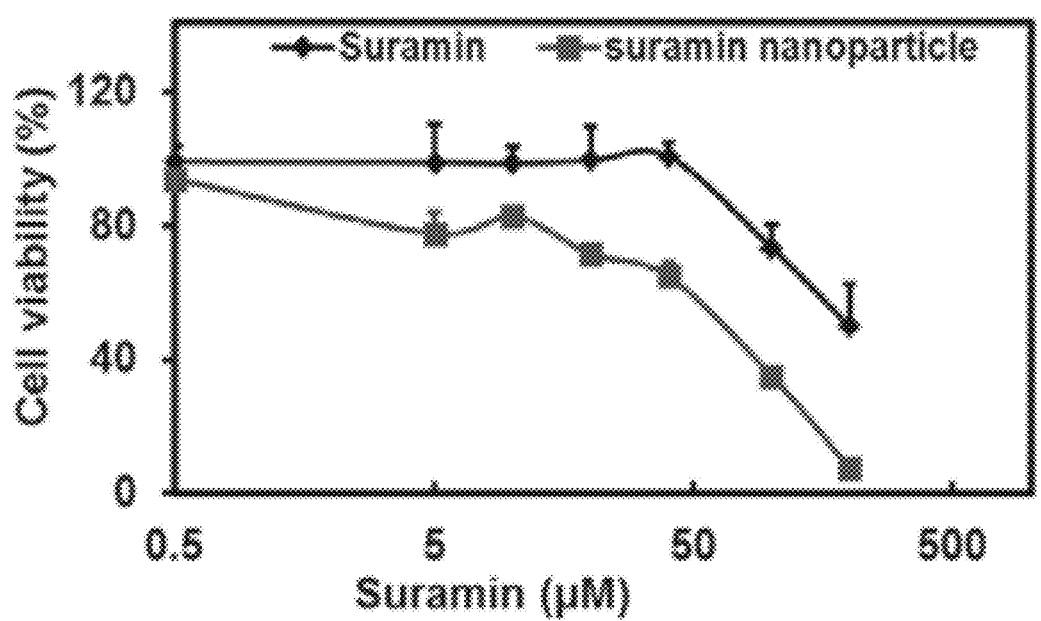
FIG. 6D is a graph illustrating the cytotoxicity of suramin and GCS-SM nanoparticles after 48 hours of treatment.
Figure 6E:
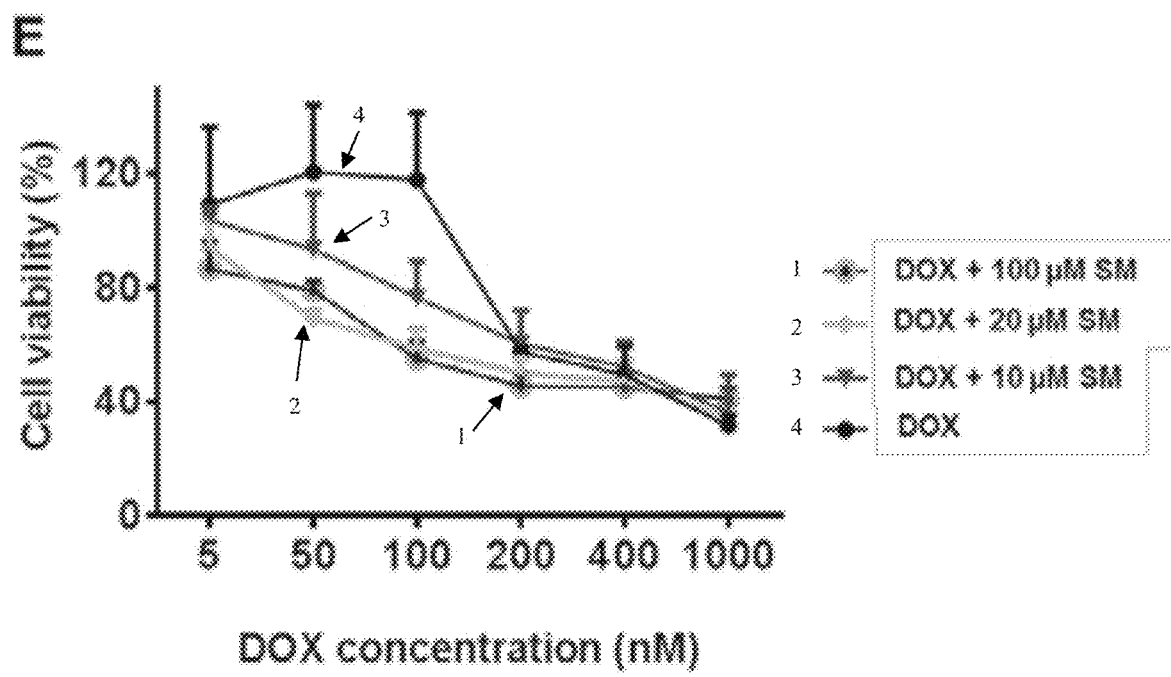
FIG. 6E is a graph illustrating the cell viability of DOX in combination with different concentrations of suramin in cells pretreated with a/b fibroblast growth factor (a/b FGF).

Since SM was reported to induce the drug cross resistance against DOX and amsacrine and cause neurologic toxicity at high concentration, determining a ratio that ensures that the combination of DOX and SM achieves a synergistic effect while not inducing side effects was critical. After 24 hours of treatment with 200 µM SM in form of either free SM or SM NPs, no cytotoxicity was observed in MDA-MB-231 cells (data not shown). However, referring to FIG. 6D, after 48 hours of treatment, the $IC_{50}$ of SM and SM NPs was 200 µM and 63 µM, respectively. In this study, SM at non-toxic doses (10 µM, 20 µM and 100 µM) when combined with DOX was tested. It was first investigated whether free-drug combinations at a non-toxic dose of SM increases DOX cytotoxicity in the presence of a/b FGF. FIG. 6E shows that the cytotoxicity of DOX was greatly enhanced by the addition of 10 µM SM, but a further increase of SM concentration (20 µM or 100 µM) did not additionally boost its cytotoxicity.

Figure 6F:
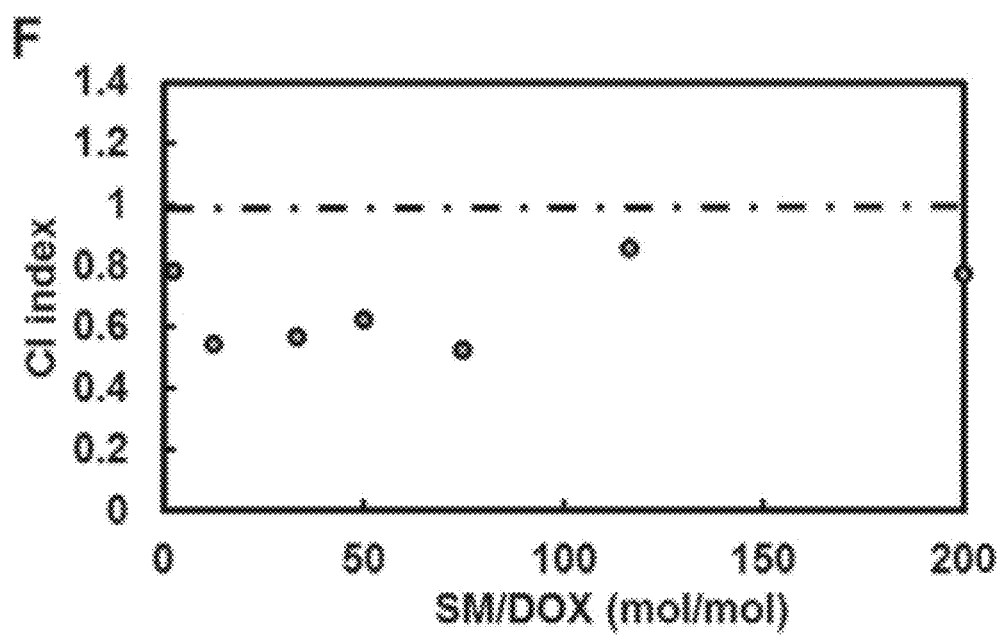
FIG. 6F is a graph illustrating is a graph illustrating the combination index (CI) of DOX and GCS-SM nanoparticles mixed at different ratios.
Figure 6G:
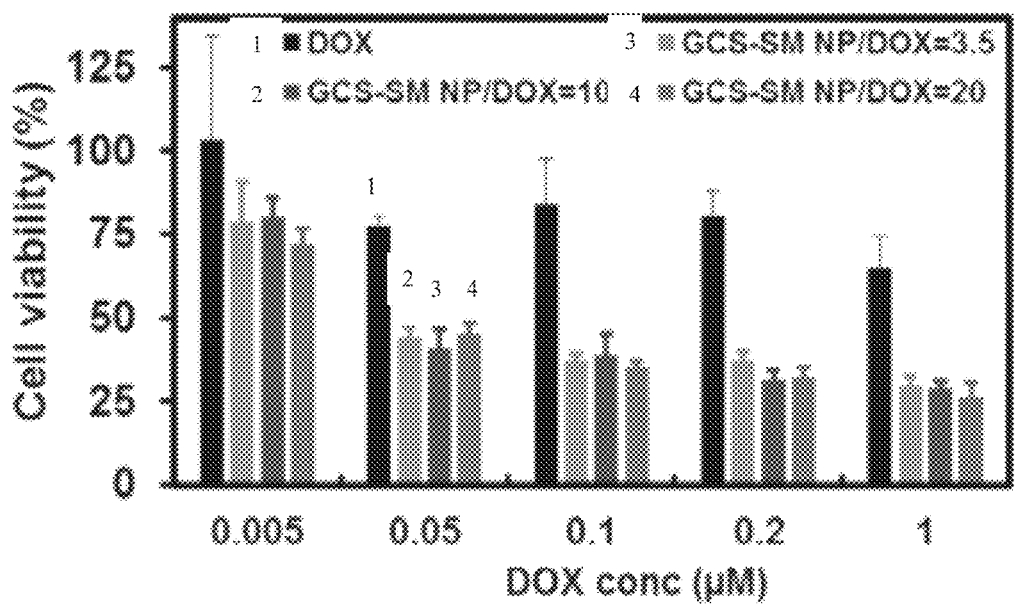
FIG. 6G is a graph illustrating the cell viability of DOX and GCS-SM/DOX nanoparticles at various ratios of SM to DOX.

SM has been reported to enter human micro-vascular endothelial cells through an active process involving the caveolae system, while a zwitterionic nanoparticle may enter a cell membrane through membrane penetration. Without intending to be limited by any particular theory, the present inventor has found that the synergistic effect is the result of the efficiency with which the SM can be delivered in the nanoparticle system of the present invention. To optimize the synergistic effect, different ratios of GCS-SM NPs to DOX were tested in MDA-MB-231 cells. The results in FIG. 6F show that synergistic growth inhibitory effects were observed at relatively low ratios of SM to DOX (Additive effect with CI=1, synergism with CI<1, and antagonism with CI>1). A profile of synergistic growth inhibition of MDA-MB-231 cells under different concentrations of SM at three different GCS-SM/DOX ratios (from 3.5 to 20) is shown in FIG. 6G.

Figure 7A:
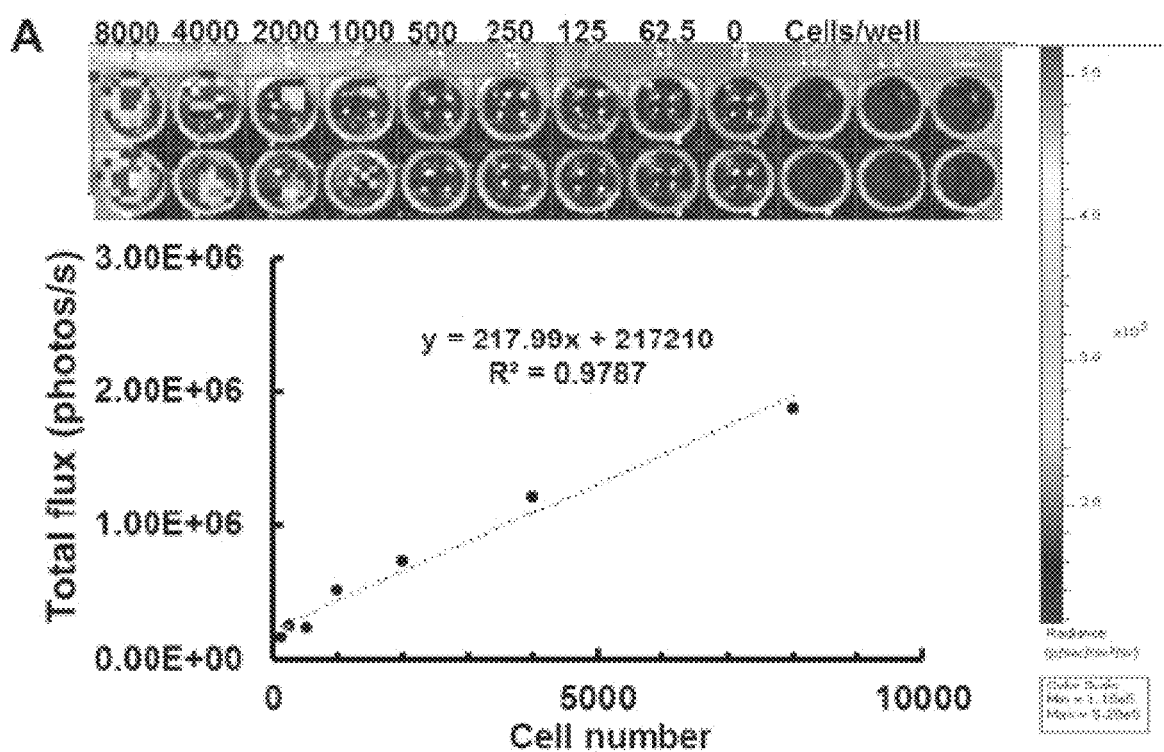
FIG. 7A includes a series of images and a graph illustrating the cell luminescence intensity as a function of cell number to show the inhibitory effect of GCS-SM/DOX nanoparticles on tumor growth in vivo.

2.6. GCS-SM/DOX NP Inhibits Proliferation and Metastasis of Cancer Cells in a Tumor-Bearing Mouse Model Based on the in vitro results, the anti-metastatic efficacy of GCS-SM/DOX NP in a breast cancer lung metastasis mouse model was further tested. There are two frequently used methods to generate breast cancer lung metastasis animal models: (1) orthotropic implantation of cancer cells in the mammary gland; and (2) tail vein injection of cancer cells. The tail vein injection method was utilized not only because it is faster but also because it yields tumors mainly in the lung tissue with similar genetic profiles. It was previously reported that if a treatment was started on the first day of cell inoculation, the number of metastasis would be greatly inhibited by the combination of chemotherapy and SM. Thus, to allow the injected cancer cells to adapt to a new environment, treatment with the nanoparticles of the present invention was initiated on the second day post cell inoculation. The effect of the combination treatment on the breast cancer lung metastasis was evaluated by bioluminescence signals in the ventral images and overall survival time. FIG. 7A shows the high sensitivity of luminescence imaging system and validated that the luminescence signal was highly correlated with cell number in the range of 125 cells/well to 8,000 cells/well.

Figure 7B:
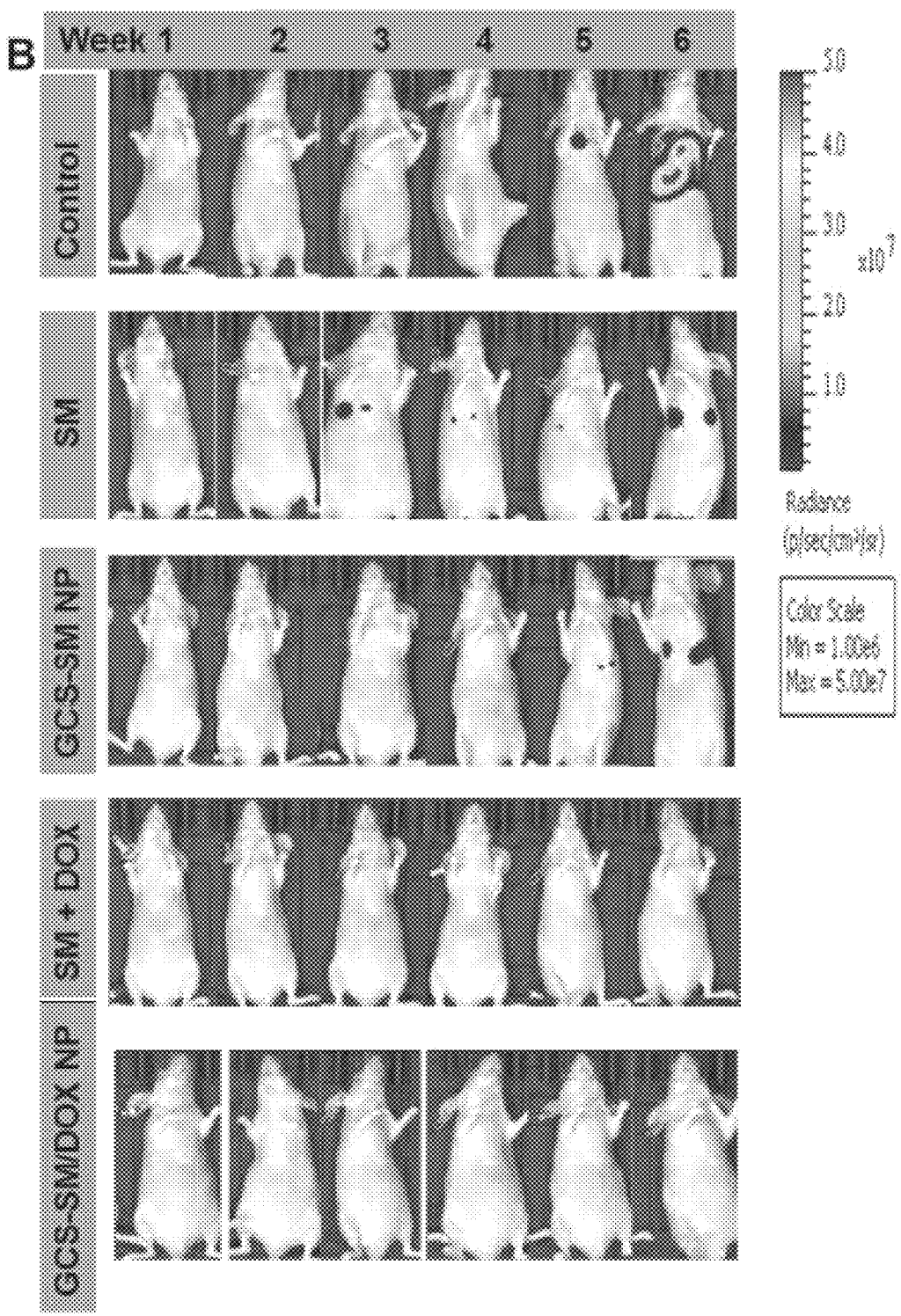
FIG. 7B shows a series of luminescence images of mice from various nanoparticle treatment groups compared to a control from 1 week to 6 weeks.
Figure 7C:
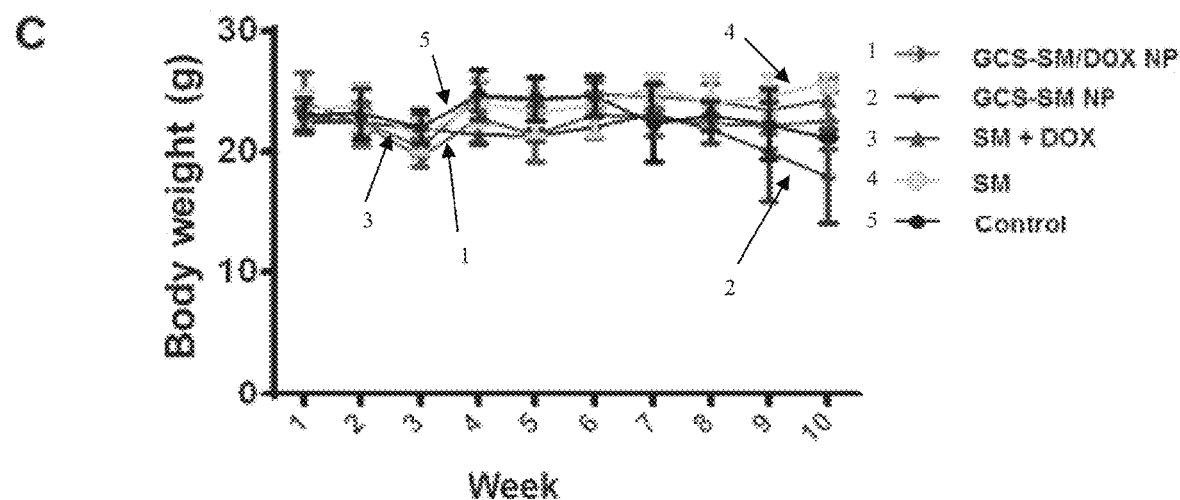
FIG. 7C is a graph illustrating the mice body weight change for various nanoparticle treatment groups compared to a control over a treatment time period of 10 weeks.
Figure 7D:
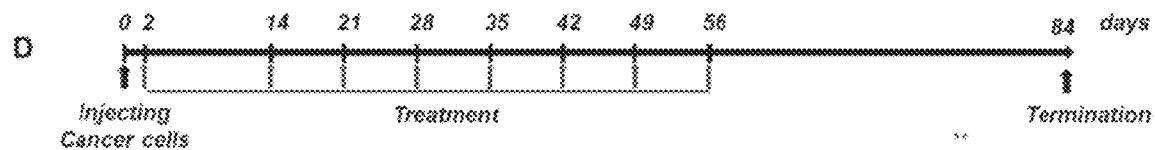
FIG. 7D is a graph illustrating the timeline of the in vivo experiments, where cancer cells were injected at Day 0 and termination occurred at Day 84.

The mice were given different treatments for 8 weeks according a predesigned schedule set forth in FIG. 7D. The whole-body photoemission rate was measured to indicate cell proliferation and the progression of tumor metastasis over the next 6 weeks, as shown in FIG. 7B. The results showed that in the control group, the luminescence lung signal associated with the MDA-MB-231 cells was dramatically increased after week 5. For the free SM and GCS-SM NP treatment groups, both the proliferation of cancer cells and metastasis were slowed down compared to the control. For the free drug combination treatment, the proliferation of cancer cells was dramatically inhibited and no detectable lung metastasis was observed during the experimental period, while the GCS-SM/DOX NPs of the present invention completely eradicated the cancer cells from the treated mice. Furthermore, the injection of the free SM, free DOX/SM combination, GCS-SM NPs, and GCS-SM/DOX NPs did not cause significant weight loss after 8 weeks of treatment, as shown in FIG. 7C.

Figure 7E:
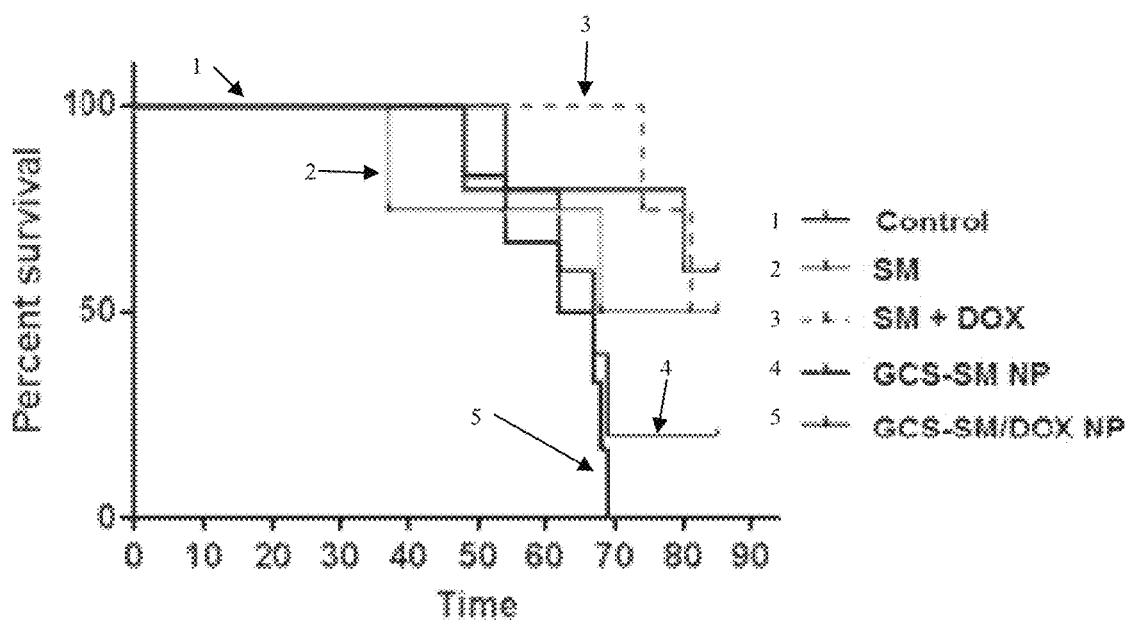
FIG. 7E is a graph showing the survive curves for various nanoparticle treatment groups compared to a control.

Next, Kaplan-Meier survival analysis was carried out at 12 weeks, as shown in FIG. 7E. The saline-treated control group showed a 0% survival rate at 68 days. The SM and GCS-SM NP treatments had moderately increased survival rates. The median survival time for the control mice was 64.5 days, while the median survival time for the SM treatment alone mice reached 76.5 days. For the free drug combination group and the GCS-SM/DOX NP group, the median survival time was significantly improved (P=0.0038 and 0.021, respectively). After week 12, the free drug combination group had a survival rate of 50%, while GCS-SM/DOX NP group had a survival rate of 60%. Correspondingly, the median survival time was extended to 81.5 days for the free drug combination group, while for GCS-SM/DOX NP treatment group, the median survival time was extended more than 85 days.

Figure 7F:
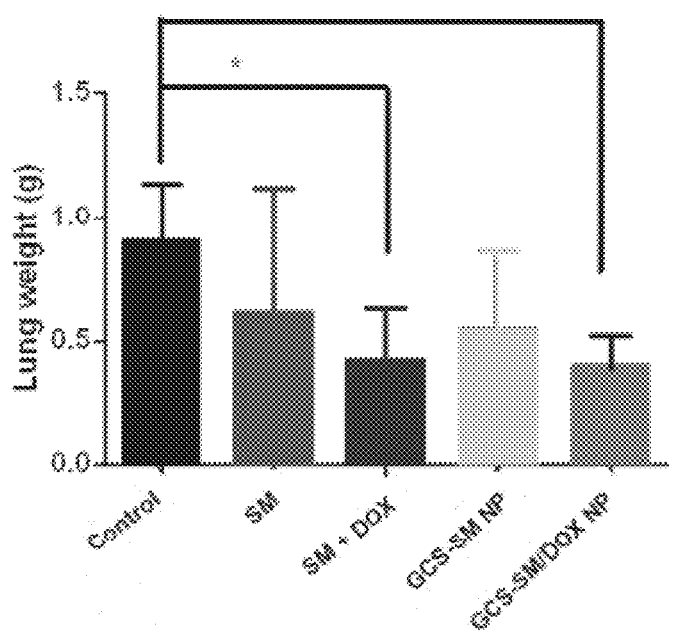
FIG. 7F is a graph illustrating the lung weight for various nanoparticle treatment groups compared to a control.

When a tail vein inoculation method was used, the metastatic sites established cell colonies instead of discrete tumors. Thus, the metastatic status of each group was further evaluated by measuring their lung weights. Neither the SM nor the GCS-SM NP groups showed significant effect on lung weight compared to the control group, while the free drug combination and the GCS-SM/DOX NP treatments reduced lung weight by 53% (P=0.022) and 56% (P=0.0089), respectively, as shown in FIG. 7F.

Figure 8A:
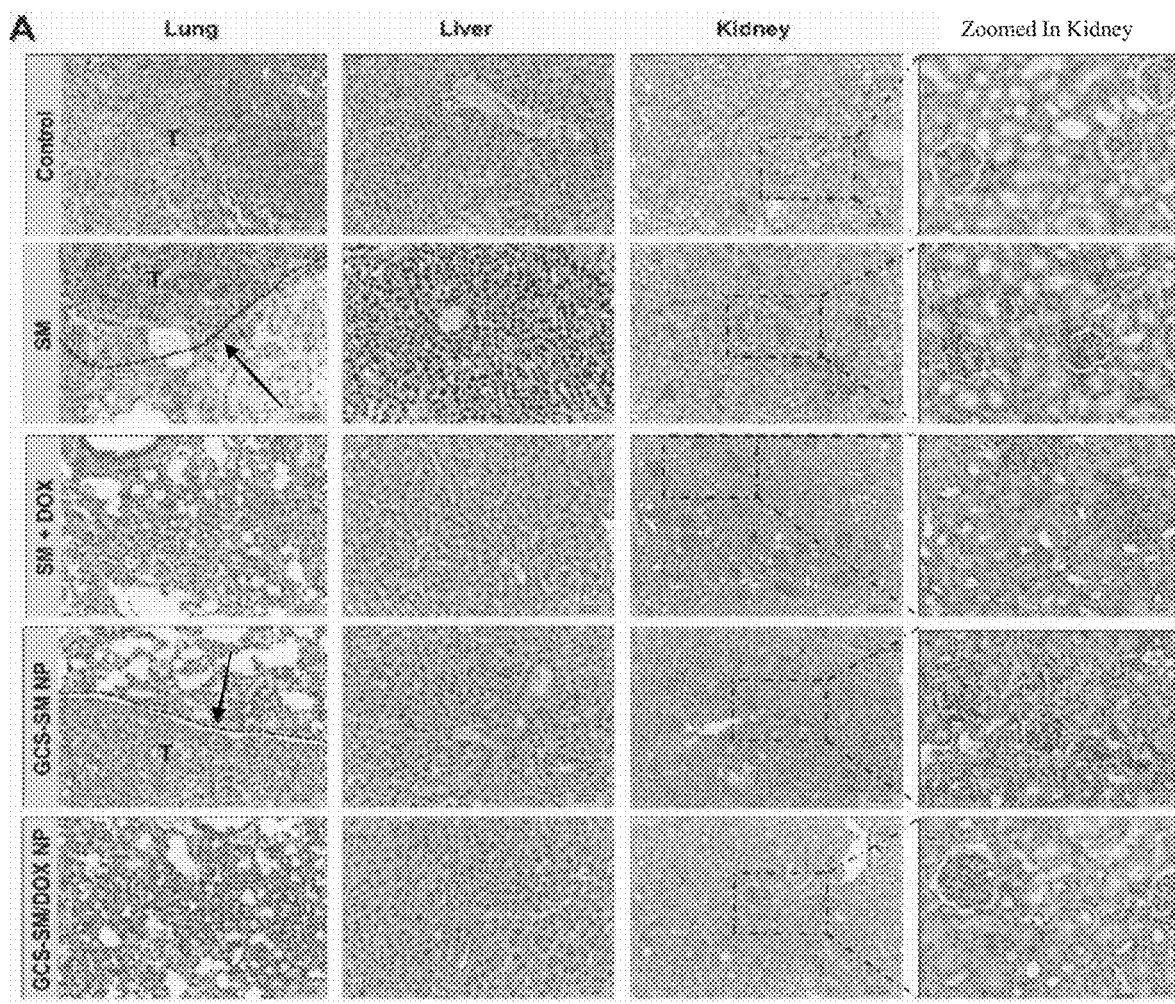
FIG. 8A shows a series of images of lungs, liver, and kidney tissue stained with hematoxylin and eosin (H&E), where black arrows indicated the tumor (T) area in the lung.

2.7. Evaluation of GCS-SM/DOX NP Treatment by Transmission Electron Microscopy, Histology and Immunohistochemistry Analysis Histological analysis of the lung, liver, and kidney from each treatment is shown in FIG. 8A. Based on the boundary between the normal tissue and tumor tissue, it was found that the lung in the control group was almost fully covered by cancer cells, while both the free SM and GCS-SM NP treated groups had a mild reduction in the occupied area ratio between the tumorous tissue and normal tissue. In the free drug combination and the GCS-SM/DOX NP groups, no visible tumor was found in their respective tissue sections. There was no significant difference in histology among the livers from all groups. However, surprisingly, the free drug combination of DOX and SM resulted in severe glomerulonephritis, where the glomeruli were surrounded by severe inflammatory infiltrate. As expected, the nanoparticles GCS-SM/DOX NP treated group showed a normal kidney histologic structure, similar as the structures shown in the control, free SM, and GCS-SM NP treated groups.

Figure 8B:
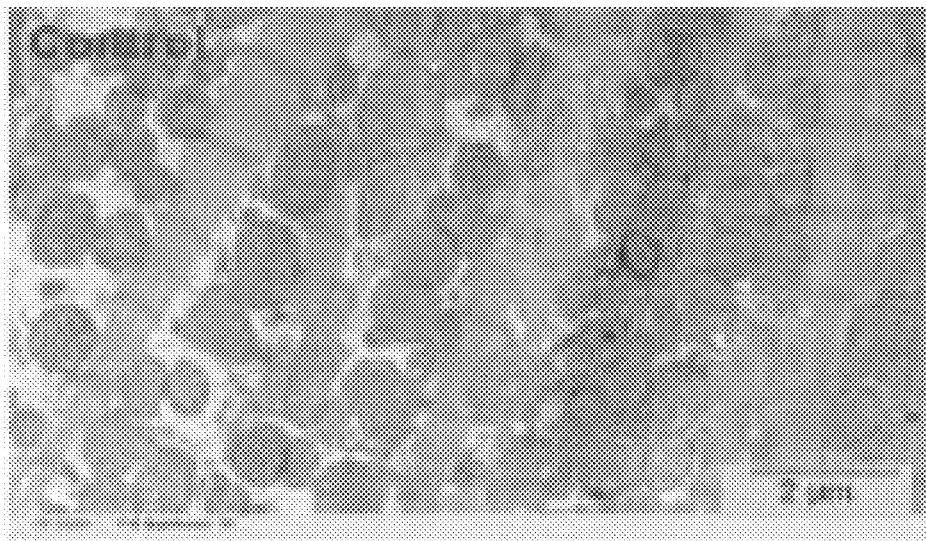
FIG. 8B is a transmission electron microscopy (TEM) image of heart tissue from a control treatment group, where the scale bar is 2 micrometers.
Figure 8C:
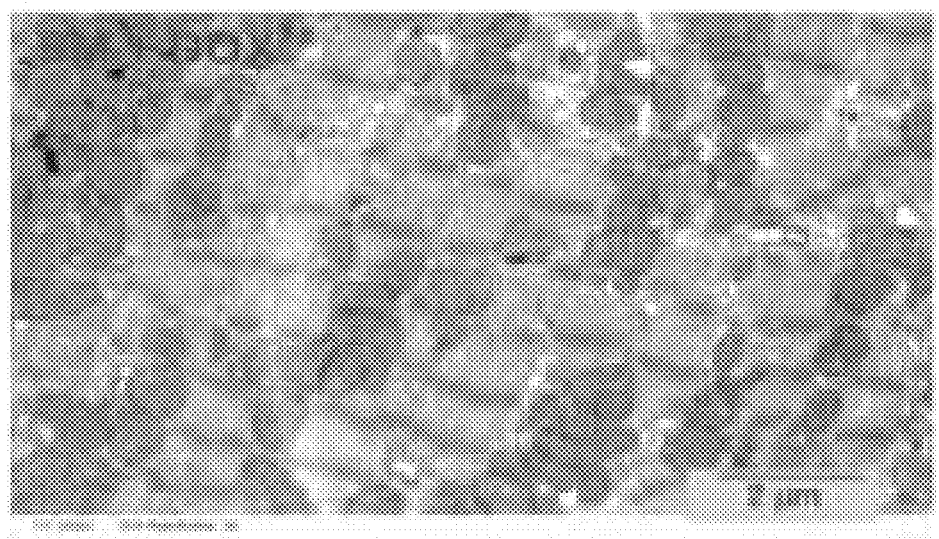
FIG. 8C is a TEM image of heart tissue from a free drug combination treatment group, where the scale bar is 2 micrometers.
Figure 8D:
FIG. 8D is a TEM image of heart tissue from a GCS-SM/DOX nanoparticle treatment group, where the scale bar is 2 micrometers.

While DOX is an effective anticancer drug, it has notorious cardiotoxic effects. It is suggested that the cardiotoxic effects primarily come from iron accumulation in mitochondria and the production of ROS. The DOX-dependent cardiac damage often results in irregular-aligned mitochondria and reduced perivascular fibrosis which can be detectable by transmission electron microscopy (TEM). Analysis of the cardiovascular pathology by TEM revealed that the free drug combination treated group exhibited misaligned mitochondria as shown in FIG. 8C compared to the control as shown in FIG. 8B, indicating the consequence of cardiotoxicity. However, no abnormal mitochondria alignment was detected in the GCS-SM/DOX NP treatment group, as shown in FIG. 8D.

Figure 8E:
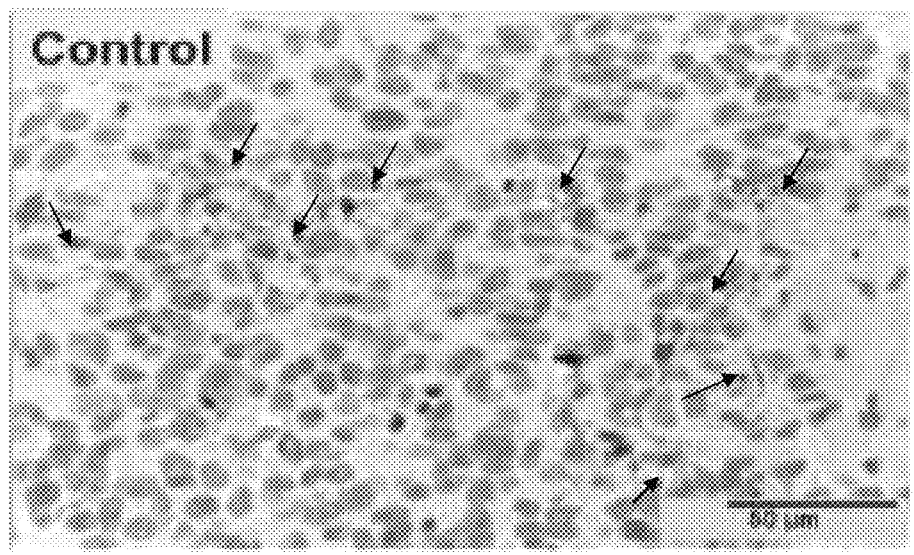
FIG. 8E is an image showing immunohistochemistry (IHC) staining from a control treatment group that was cut into a 5-micrometer thick section, stained with CD31, and imaged, where the scale bar is 50 micrometers, where the arrows refer to microvessels, and where the dark/brown stained sections are tumor blood vessels.
Figure 8F:
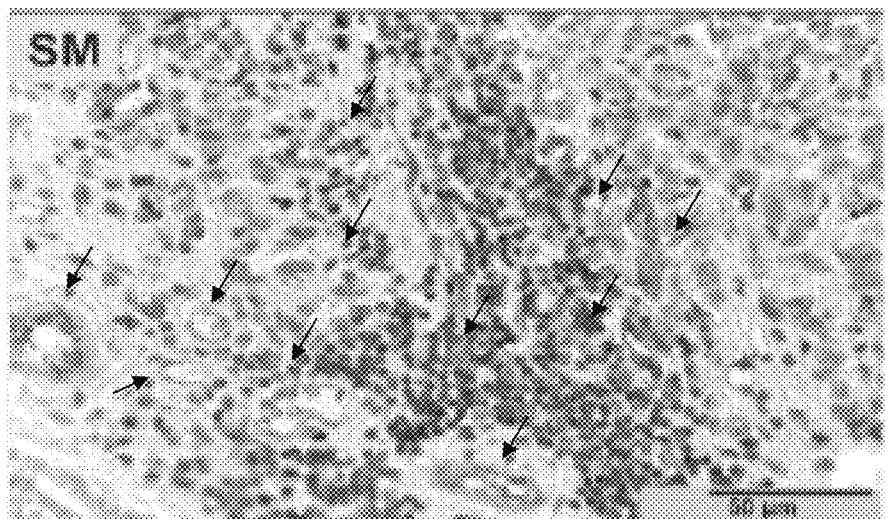
FIG. 8F is an image showing immunohistochemistry (IHC) staining from a suramin treatment group that was cut into a 5-micrometer thick section, stained with CD31, and imaged, where the scale bar is 50 micrometers, where the arrows refer to microvessels, and where the dark/brown stained sections are tumor blood vessels.
Figure 8G:
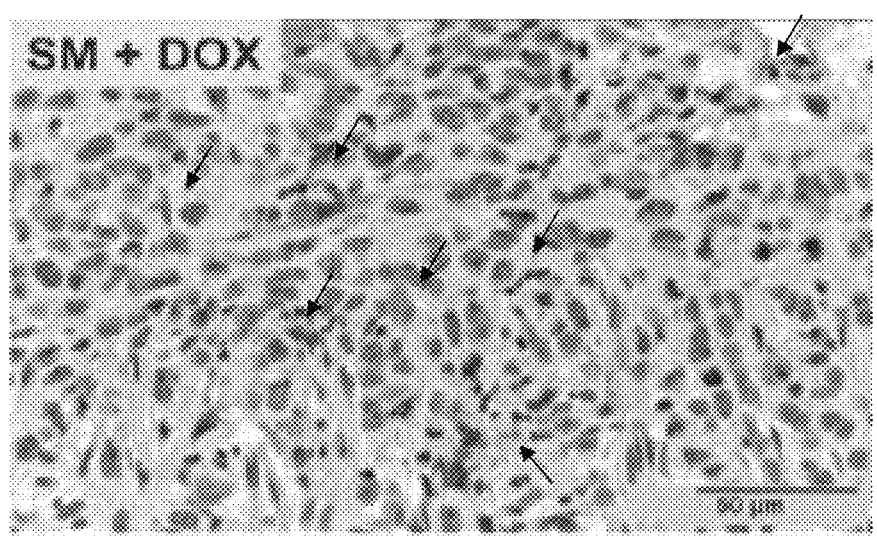
FIG. 8G is an image showing immunohistochemistry (IHC) staining from a suramin and doxorubicin treatment group that was cut into a 5-micrometer thick section, stained with CD31, and imaged, where the scale bar is 50 micrometers, where the arrows refer to microvessels, and where the dark/brown stained sections are tumor blood vessels.
Figure 8H:
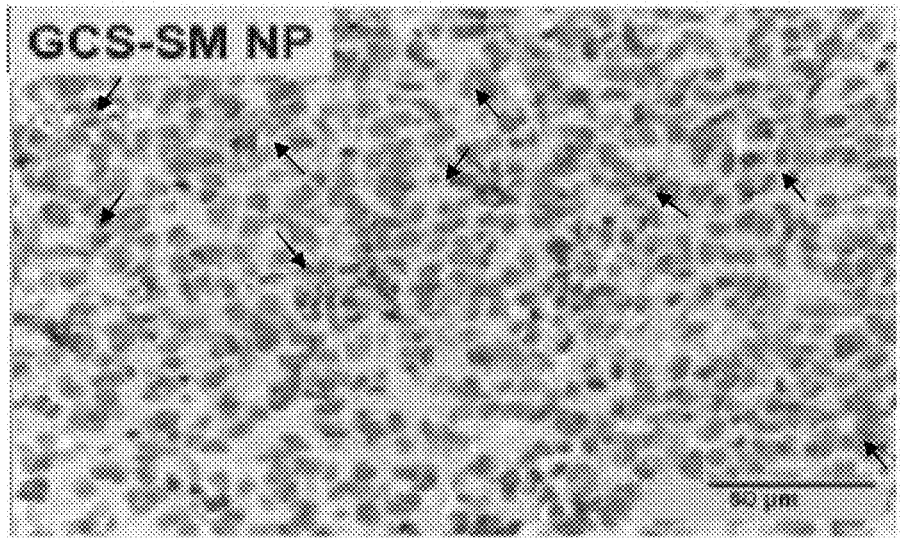
FIG. 8H is an image showing immunohistochemistry (IHC) staining from a GCS-SM nanoparticle treatment group that was cut into a 5-micrometer thick section, stained with CD31, and imaged, where the scale bar is 50 micrometers, where the arrows refer to microvessels, and where the dark/brown stained sections are tumor blood vessels.
Figure 8I:
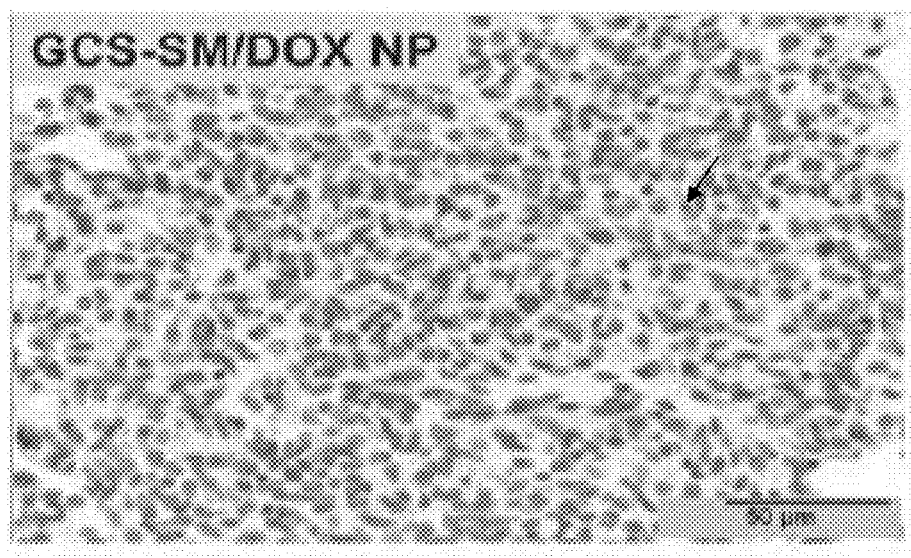
FIG. 8I is an image showing immunohistochemistry (IHC) staining from a GCS-SM/DOX nanoparticle treatment group that was cut into a 5-micrometer thick section, stained with CD31, and imaged, where the scale bar is 50 micrometers, where the arrows refer to microvessels, and where the dark/brown stained sections are tumor blood vessels.
Figure 8J:
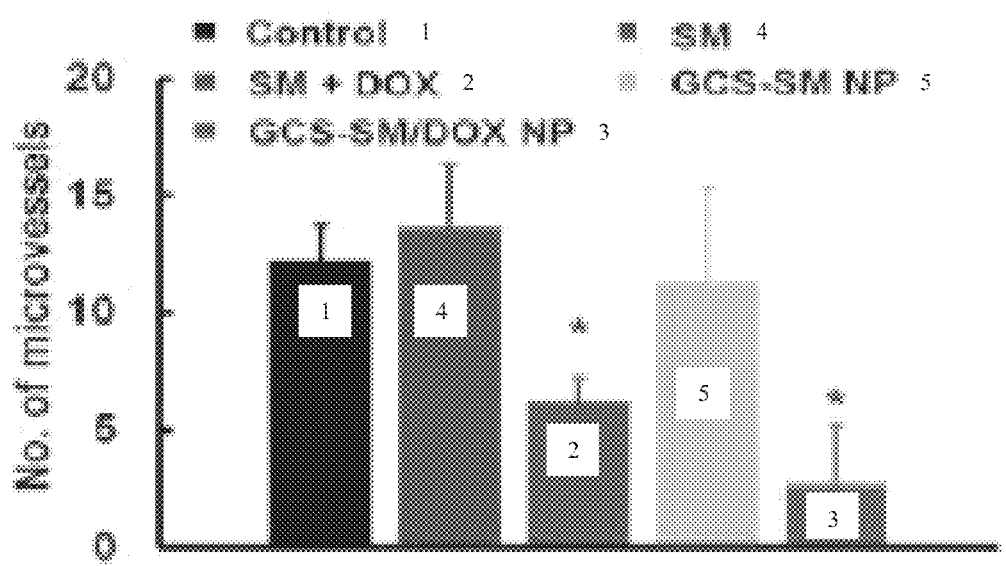
FIG. 8J is a graph illustrating the number of microvessels formed for the various treatment groups compared to a control.

It has been reported that SM inhibits tumor growth partially through its anti-angiogenesis effects. Thus, the tumor neo-vasculature was evaluated with IHC by examining the density of CD31 stained microvessels in tumor tissues from the different treatment groups, as shown in FIG. 8E (control), FIG. 8F (free SM), FIG. 8G (free SM and DOX), FIG. 8H (GCS-SM NP), and FIG. 8I (GCS-SM/DOX NP). Different from other reports, the IHC analysis showed that SM alone did not decrease the formation of new blood vessels, which may due to the relative low SM concentration used in the in vivo study. It was however revealed that the GCS-SM/DOX NP and the free drug combination of SM and DOX can significantly reduce the number of newly formed microvessels in tumor tissues as shown in FIG. 8J, suggesting that the increase in the survival rate of mice in those groups could partially attribute to the anti-angiogenesis effect of the drug combination.

3. Discussion

Cancer cell migration and metastasis significantly reduce the survival rate of breast cancer patients. Therefore, an effect approach to control circulating tumor cells (CTC) and prevent them from forming tumors at remote sites, such as in the lungs, liver, brain, and bone, is crucial in fighting against breast cancer. Research has found that triple negative breast cancer (TNBC) is more prone to spread to other organs after treatment. Thus, the TNBC lung metastasis model was adopted in this study.

With the help of TPP, chitosan has been formulated into various nanoparticles through ionotropic gelation for the delivery of active pharmaceutical ingredients. TPP is a gelating agent and serves as a non-active excipient in those dosages. SM, a century-old drug that has been approved for the treatment of African sleeping sickness and river blindness, was recently proposed to sensitize chemotherapy drugs for the treatment of many types of cancers both in mouse models and in clinical trials. Since the structure of SM contains six negatively charged sulfonic acid groups, its use as a dual functional agent in the formulation of DOX loaded nanoparticles was proposed, where the SM served as not only a gelating agent but also an active pharmaceutical ingredient.

When negatively charged SM was mixed with positively charged GCS, size controllable GCS-SM nanoparticles (having an average particle size of about 200 nm) formed spontaneously as shown in FIGS. 3A and 3B. The nanogel was slightly positively charged and stable in both PBS and serum containing environments, indicating it could be a good drug carrier for in vivo applications. As shown in FIG. 3C, both DOX and SM had sustained release from the nanoparticles over 8 hours, which is much slower than the release of the free versions of the drugs (about 75% release of free DOX within 1 hour).

The nanoparticle form of SM (GCS-SM NPs) showed better anti-migration and anti-invasion effects than free SM as shown in FIGS. 4A-4F. Further, both the free SM and GCS-SM NP treatments resulted in decreased tube number and tube length in a cultured HUVEC cell assay as shown in FIGS. 5A-5D, suggesting that the combination of GCS-SM has anti-angiogenesis effects in vitro. The MTT assay found that the combination of DOX and SM shows a synergetic effect in killing MDA-MB-231 cells over a wide range of concentrations, as shown in FIGS. 4E-4F. In the cellular uptake study, the cells were treated with a/b FGF to induce drug resistance. Free DOX was transported into the cells through diffusion, however, the p-gp overexpressed on the membrane of the drug resistant cells can pump out the free DOX quickly. In contrast, nanoparticles have the potential to overcome drug resistance, since they can bypass p-gp though endocytosis. As shown in FIGS. 6A-6G, the GCS-SM/DOX NPs of the present invention enhanced the cytotoxicity of DOX by counteracting the effect of the a/b FGFs, which was due to the boosted cellular uptake of the DOX-loaded nanoparticle as compared with free DOX alone.

To evaluate the anticancer effect of the GCS-SM/DOX NPs of the present invention, a breast cancer lung metastatic mouse model was adopted. In vivo imaging revealed that both GCS-SM/DOX NPs and the combination of free SM and DOX could effectively inhibit the growth of lung metastatic tumor after 6 weeks of treatment, as show in FIG. 7B. In addition, the GCS-SM/DOX NPs and the free drug combination extended the median survival time from 64.5 days to 85.0 days and 81.5 days, respectively, as shown in FIG. 7E. Correspondingly, the lung weights (tumor burdens) of those two treatment groups were significantly lower than that of the control group, as shown in FIG. 7F. Meanwhile, the immunohistochemistry results of CD31 staining shown in FIG. 8I suggests that reduced tumor burden in the GCS-SM/DOX NPs and the free drug combination groups was at least partially attributed to their potent anti-angiogenesis effects.

It has been reported in many studies that the use of DOX and SM cause cardiotoxicity and renal damage. To study the potential systemic toxicity of the GCS-SM/DOX NP treatment, both histology analysis and TEM were carried out at the end of the treatment. Although both the GCS-SM/DOX NP and its free drug counterpart exhibited similar tumor growth inhibitory effect, FIGS. 8A and 8D revealed that no abnormal feature was identified in the tissues of the GCS-SM/DOX NP treated group, while the free drug combination induced significant toxicity in both kidney and heart, as evidenced by the glomerulonephritis in the kidney and the damaged mitochondria in cardiomyocytes present for the free drug combination treatment groups shown in FIGS. 8A and 8C. Therefore, the GCS-SM/DOX NP system can eliminate the cardio and renal toxicities associated with the combination of free DOX and free SM. In conclusion, the GCS-SM/DOX ternary nanoparticle system contemplated by the present invention could be a safe and effective tool for preventing and treating TNBC lung metastasis.

4. Conclusion

In summary, a GCS based dual-payload nanocarrier system was developed that contains an anti-angiogenesis drug (SM) and a chemotherapeutic drug (DOX). The repurposed SM serves as a gelator for the formation of the nanoparticle as well as an active pharmaceutical ingredient to sensitize cancer cells, inhibit migration and invasion of cancer cells, as well as block neovascularization in vitro. In vivo experiments proved that the GCS-SM/DOX NP system of the present invention could greatly inhibit breast cancer lung metastases and improve the survival time for mice while not inducing the cardiotoxicity and renal toxicity associated with its free drug counterpart. Due to the simplicity of the nanoparticle preparation procedure, the developed system could be easily scaled up and further tested in a clinical setting.

These and other modifications and variations to the present invention may be practiced by those of ordinary skill in the art, without departing from the spirit and scope of the present invention, which is more particularly set forth in the appended claims. In addition, it should be understood the aspects of the various embodiments may be interchanged both in whole or in part. Furthermore, those of ordinary skill in the art will appreciate that the foregoing description is by way of example only, and is not intended to limit the invention so further described in the appended claims.

What is claimed is:

1. A nanoparticle system comprising a plurality of nanoparticles, where each of the nanoparticles comprises a biodegradable matrix, a polysulphonated naphthylurea, and a chemotherapeutic agent, wherein each of the nanoparticles has a diameter ranging from about 20 nanometers to about 400 nanometers, wherein a ratio of the concentration of the polysulphonated naphthylurea to the concentration of the chemotherapeutic agent ranges from about 2 to about 100.

2. The nanoparticle system of claim 1, wherein the biodegradable matrix comprises a natural polysaccharide, a protein, a peptide, or a derivative thereof.

3. The nanoparticle system of claim 2, wherein the biodegradable matrix comprises glycol chitosan, chitosan, collagen, gelatin, or protamine.

4. The nanoparticle system of claim 1, wherein the polysulphonated naphthylurea comprises suramin or a pharmaceutically acceptable salt thereof.

5. The nanoparticle system of claim 4, wherein the polysulphonated naphthylurea comprises suramin sodium salt.

6. The nanoparticle system of claim 1, wherein the chemotherapeutic agent comprises an anthracycline.

7. The nanoparticle system of claim 6, wherein the chemotherapeutic agent comprises doxorubicin.

8. The nanoparticle system of claim 1, the polysulphonated naphthylurea is present at a concentration ranging from about 0.1 micromolar to about 200 micromolar.

9. The nanoparticle system of claim 1, wherein the chemotherapeutic agent is present at a concentration ranging from about 0.025 micromolar to about 20 micromolar.

10. A method of forming a nanoparticle system, the method comprising:
    forming a first solution comprising a first water-based salt solution having a pH ranging from about 6 to about 7.2 and a biodegradable matrix;
    forming a second solution comprising a second water-based salt solution having a pH ranging from about 6 to about 7.2 and a polysulphonated naphthylurea or a pharmaceutically acceptable salt thereof;
    forming a third solution comprising double-distilled water and a chemotherapeutic agent, wherein a ratio of the concentration of the polysulphonated naphthylurea or a pharmaceutically acceptable salt thereof to the concentration of the chemotherapeutic agent ranges from about 2 to about 100;
    combining the second solution and the third solution to form a fourth solution; and
    adding the fourth solution to the first solution to form a plurality of nanoparticles.

11. The method of claim 10, wherein the biodegradable matrix comprises a natural polysaccharide, a protein, a peptide, or a derivative thereof.

12. The method of claim 10, wherein the polysulphonated naphthylurea comprises suramin or a pharmaceutically acceptable salt thereof.

13. The method of claim 10, wherein the chemotherapeutic agent comprises an anthracycline.

14. The method of claim 10, wherein the concentration of the biodegradable matrix in the first solution ranges from about 1 milligram/milliliter to about 4 milligrams/milliliter.

15. The method of claim 10, wherein the concentration of the polysulphonated naphthylurea in the second solution ranges from about 0.08 milligrams/milliliter to about 0.7 milligrams/milliliter.

16. The method of claim 10, wherein the concentration of the chemotherapeutic agent in the third solution ranges from about 0.25 milligrams/milliliter to about 2 milligrams/milliliter.

17. A method of treating cancer in a mammal, the method comprising:
    introducing a nanoparticle system comprising a plurality of nanoparticles to a cancerous tumor in tissue of the mammal, wherein each of the plurality of nanoparticles comprises a biodegradable matrix, a polysulphonated naphthylurea, and a chemotherapeutic agent, wherein each of the nanoparticles has a diameter ranging from about 20 nanometers to about 400 nanometers, wherein a ratio of the concentration of the polysulphonated naphthylurea to the concentration of the chemotherapeutic agent ranges from about 2 to about 100.

18. The method of claim 17, wherein the biodegradable matrix comprises a natural polysaccharide, a protein, a peptide, or a derivative thereof, wherein the polysulphonated naphthylurea comprises suramin or a pharmaceutically acceptable salt thereof, and wherein the chemotherapeutic agent comprises an anthracycline.

* * * * *